US011364710B2

United States Patent
Jimbo et al.

(10) Patent No.: US 11,364,710 B2
(45) Date of Patent: Jun. 21, 2022

(54) COMPOSITION, FILM, GLASS ARTICLE, COMPOUND, HIGH PURITY COMPOSITION, METHOD FOR PRODUCING COMPOUND, AND METHOD FOR PRODUCING FILM

(71) Applicant: FUJIFILM Corporation, Tokyo (JP)

(72) Inventors: Yoshihiro Jimbo, Shizuoka (JP); Jun Tanabe, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 102 days.

(21) Appl. No.: 16/027,257

(22) Filed: Jul. 3, 2018

(65) Prior Publication Data

US 2018/0311936 A1 Nov. 1, 2018

Related U.S. Application Data

(63) Continuation of application No. PCT/JP2016/087883, filed on Dec. 20, 2016.

(30) Foreign Application Priority Data

Jan. 12, 2016 (JP) .............................. JP2016-003200
Apr. 15, 2016 (JP) .............................. JP2016-082112

(51) Int. Cl.
*C08L 83/04* (2006.01)
*B32B 17/10* (2006.01)
(Continued)

(52) U.S. Cl.
CPC ........ *B32B 17/10798* (2013.01); *B32B 17/06* (2013.01); *B32B 27/283* (2013.01); *C03C 17/009* (2013.01); *C07D 339/06* (2013.01); *C07F 7/04* (2013.01); *C07F 7/18* (2013.01); *C07F 7/1804* (2013.01); *C08L 83/04* (2013.01);
(Continued)

(58) Field of Classification Search
None
See application file for complete search history.

(56) References Cited

U.S. PATENT DOCUMENTS 3,694,211 A * 9/1972 Sato ..................... C07D 339/06
430/512
4,321,400 A 3/1982 Ashby
(Continued)

FOREIGN PATENT DOCUMENTS

CN 102137910 7/2011
EP 2116585 11/2009
(Continued)

OTHER PUBLICATIONS

Li Hongqi, Bull. Chem. Soc. Japan.,74 , 1717-1725 (2001).*
(Continued)

*Primary Examiner* — Kenneth J Stachel
(74) *Attorney, Agent, or Firm* — JCIPRNET

(57) ABSTRACT

Provided are a composition which includes a compound having a benzodithiol structure and a compound having an —O—Si—O— structure and is capable of forming a film that has long-wavelength ultraviolet range shielding properties, high pencil hardness and good light fastness; a film; a glass article; a compound; a high purity composition; a method for producing a compound; and a method for producing a film.

6 Claims, 1 Drawing Sheet

(51) Int. Cl.
*C09D 183/04* (2006.01)
*B32B 17/06* (2006.01)
*C09D 7/40* (2018.01)
*C07F 7/18* (2006.01)
*C03C 17/00* (2006.01)
*C07F 7/04* (2006.01)
*B32B 27/28* (2006.01)
*C07D 339/06* (2006.01)
*C08J 3/075* (2006.01)

(52) U.S. Cl.
CPC ............ *C09D 7/40* (2018.01); *C09D 183/04* (2013.01); *C03C 2217/74* (2013.01); *C03C 2217/78* (2013.01); *C03C 2218/113* (2013.01); *C08J 3/075* (2013.01); *C08L 2203/16* (2013.01)

(56) References Cited

U.S. PATENT DOCUMENTS

| | | | |
|---|---|---|---|
| 4,555,559 | A | 11/1985 | Kimura et al. |
| 5,391,795 | A | 2/1995 | Pickett |
| 2002/0115753 | A1 | 8/2002 | Ravichandran et al. |
| 2010/0025642 | A1 | 2/2010 | Hanaki et al. |
| 2010/0076124 | A1 | 3/2010 | Yawata et al. |
| 2010/0130638 | A1 | 5/2010 | Hanaki et al. |
| 2010/0210762 | A1* | 8/2010 | Hanaki .............. A61Q 17/04 524/83 |
| 2011/0059033 | A1* | 3/2011 | Kitagawa ............ A61Q 17/04 424/60 |
| 2011/0120635 | A1* | 5/2011 | Jokisch ............... B32B 27/30 156/242 |
| 2011/0155976 | A1* | 6/2011 | Furukawa ............. C09D 5/32 252/589 |
| 2012/0094127 | A1 | 4/2012 | Meyer Zu Berstenhorst et al. |
| 2013/0071669 | A1 | 3/2013 | Kodaira et al. |
| 2015/0144198 | A1* | 5/2015 | Irwin ................. H01G 9/2059 136/263 |

FOREIGN PATENT DOCUMENTS

| | | |
|---|---|---|
| EP | 2301519 | 3/2011 |
| EP | 2330171 | 6/2011 |
| JP | H0314862 | 2/1991 |
| JP | H0362177 | 9/1991 |
| JP | H07278525 | 10/1995 |
| JP | 11322764 A * | 11/1999 |
| JP | 2004505984 | 2/2004 |
| JP | 2007246872 A * | 9/2007 |
| JP | 2008297228 | 12/2008 |
| JP | 2009067876 | 4/2009 |
| JP | 2009096971 | 5/2009 |
| JP | 2010095661 | 4/2010 |
| JP | 2010180288 | 8/2010 |
| JP | 2012526159 | 10/2012 |
| KR | 20110065454 | 6/2011 |
| WO | 2008105301 | 9/2008 |
| WO | 2008123504 | 10/2008 |
| WO | 2009022736 | 2/2009 |
| WO | 2009123153 | 10/2009 |
| WO | 2009123154 | 10/2009 |
| WO | 2010024441 | 3/2010 |
| WO | 2011142463 | 11/2011 |

OTHER PUBLICATIONS

English machine translation of JP2007246872 (2007).*
English machine translation of JPH11322764 (1999).*
"International Search Report (Form PCT/ISA/210) of PCT/JP2016/087883," dated Feb. 7, 2017, with English translation thereof, pp. 1-11.
"Written Opinion of the International Searching Authority (Form PCT/ISA/237) of PCT/JP2016/087883," dated Feb. 7, 2017, with English translation thereof, pp. 1-13.
Shin-Etsu Chemical Co., Ltd., "X-21-5250 Trimethylsiloxysilicate", ShinEtsu Technical Data Sheet, May 2016, pp. 1-2.
"Search Report of Europe Counterpart Application", dated Nov. 26, 2018, p. 1-p. 9.
"Office Action of Korea Counterpart Application," with English translation thereof, dated Aug. 9, 2019, p. 1-p. 15.
"Decision of Rejection of Korea Counterpart Application," with English translation thereof, dated Feb. 7, 2020, p. 1-p. 7.
Office Action of Japan Counterpart Application, with English translation thereof, dated Jul. 30, 2019, pp. 1-9.
"Office Action of China Counterpart Application", dated May 11, 2020, with English translation thereof, pp. 1-12.

* cited by examiner

COMPOSITION, FILM, GLASS ARTICLE, COMPOUND, HIGH PURITY COMPOSITION, METHOD FOR PRODUCING COMPOUND, AND METHOD FOR PRODUCING FILM

CROSS-REFERENCE TO RELATED APPLICATIONS

This application is a Continuation of PCT International Application No. PCT/JP2016/087883, filed on Dec. 20, 2016, which claims priority under 35 U.S.C. Section 119(a) to Japanese Patent Application No. 2016-003200 filed on Jan. 12, 2016 and Japanese Patent Application No. 2016-082112 filed on Apr. 15, 2016. Each of the above applications is hereby expressly incorporated by reference, in its entirety, into the present application.

BACKGROUND OF THE INVENTION

1. Field of the Invention

The present invention relates to a composition, a film, a glass article, a compound, a high purity composition, a method for producing a compound, and a method for producing a film.

2. Description of the Related Art

Ultraviolet absorbers with long wavelength absorption have been conventionally desired, but few are able to absorb up to the long wavelength ultraviolet (UV-A) range of 320 to 400 nm. In the case of preparing a material capable of absorbing up to the long wavelength ultraviolet range, two ways have been considered, one being using an ultraviolet absorber whose absorption maximum wavelength is in the long wavelength ultraviolet range and the other one being increasing the concentration of an ultraviolet absorber with short wavelength absorption.

It has also been studied to form a sol-gel film on a glass substrate in order to impart an ability to absorb ultraviolet rays to the glass substrate and impart durability such as abrasion resistance. The formation of a sol-gel film has been proposed for applications for windowpanes for building materials used in buildings such as houses and buildings, windowpanes for vehicles such as automobiles and electric trains, and the like.

In order to obtain a sol-gel film having an ability to absorb long wavelength ultraviolet rays and high abrasion resistance (hardness), various investigations have conventionally been made. For example, there is known a method of forming an ultraviolet absorbing sol-gel film on a substrate by using a coating liquid in which an ultraviolet absorber is blended in alkoxysilane.

The sol-gel film containing an ultraviolet absorber can be obtained by silanol condensation of a precursor constituted of a hydrolyzate of alkoxysilane and curing the resulting condensate by a crosslinking reaction. An example of introducing a reactive group (silane coupling group) that causes such silanol condensation into an ultraviolet absorber has also been known.

JP2009-96971A discloses a polymer material containing a benzodithiol derivative in any one of an acrylic acid-based polymer, a polyester-based polymer, and a polycarbonate-based polymer.

WO2011/142463A discloses a coating liquid for forming an ultraviolet absorbing film, containing a silicon oxide-based matrix material component constituted of at least one compound selected from hydrolyzable silicon compounds, an ultraviolet absorber, an acid having a pKa of a first proton of 1.0 to 5.0, and water. The pKa of the first proton represents the logarithm ($-Log_{10}Ka$) of the dissociation constant (Ka) of the first proton of the acid.

JP1991-14862B (JP-H03-14862B), JP1991-62177B (JP-H03-62177B), JP1995-278525A (JP-H07-278525A), JP2012-526159A, and JP2004-505984A disclose compounds in which a reactive group is introduced into an ultraviolet absorber having a benzophenone skeleton, a triazine skeleton, and a benzotriazole skeleton.

SUMMARY OF THE INVENTION

It is desired that the ultraviolet absorber has a small amount of decrease in ultraviolet absorption ability with the elapse of time in the case of being irradiated with light (ultraviolet rays), that is, it has high light fastness. The light fastness of the ultraviolet absorber can be expressed in terms of the residual amount of the ultraviolet absorber in the case where the material containing the ultraviolet absorber is irradiated with light (ultraviolet rays).

In the ultraviolet absorber, those having an absorption maximum wavelength in the long wavelength ultraviolet range have a disadvantage that the light fastness is poor and the ultraviolet absorption ability decreases with the elapse of time. On the other hand, benzophenone-based or benzotriazole-based ultraviolet absorbers are relatively excellent in light fastness although they absorb short wavelengths, so studies have been made to increase the concentration of ultraviolet absorbers. However, usually, in the case where these ultraviolet absorbers are applied in admixture with a resin (polymer material) or the like, the film thickness is limited to about several tens of μm. In order to be able to absorb the long wavelength range with this film thickness, it is necessary to add an ultraviolet absorber at a high concentration. In such a case, there was a problem that precipitation of an ultraviolet absorber and bleed-out caused by long-term use occurred.

In addition, in the case where an ultraviolet absorbing sol-gel film is formed on a glass substrate, a conventionally known ultraviolet absorber is used to absorb ultraviolet rays of long wavelengths, but this conventionally known ultraviolet absorber has problems such as poor light fastness, low hardness, and occurrence of bleed out. Therefore, an ultraviolet absorbing sol-gel film which absorbs long wavelength ultraviolet rays and has good light fastness and high hardness is required.

Compounds having a benzophenone skeleton, a triazine skeleton, and a benzotriazole skeleton are known as ultraviolet absorbers, but these ultraviolet absorbers have absorption maximum wavelengths as short wavelengths and a low long-wavelength ultraviolet ray (UV-A) shielding ability. Further, these ultraviolet absorbers have low fastness to ultraviolet rays and exhibit a disadvantage of lowered ultraviolet absorption ability in long-term use, that is, a drawback of poor light fastness.

The invention disclosed in JP2009-96971A has not been applied to a sol-gel film. Therefore, according to the invention disclosed in JP2009-96971A, it is difficult to produce a high strength film.

The invention disclosed in WO2011/142463A has room for further improvement in the light fastness of an ultraviolet absorber.

The inventions disclosed in JP1991-14862B (JP-H03-14862B), JP1991-62177B (JP-H03-62177B), JP1995-

278525A (JP-H07-278525A), and JP2012-526159A exhibit absorption maximum wavelengths as short wavelengths due to being derived from the skeleton of an ultraviolet absorber, a low shielding ability against long wavelength ultraviolet rays (UV-A), and furthermore low fastness to ultraviolet rays.

An object of the present invention is to provide a composition capable of providing a film having long-wavelength ultraviolet range shielding properties, high pencil hardness, and good light fastness.

Another object of the present invention is to provide a film formed from a composition capable of providing a film having long-wavelength ultraviolet range shielding properties, high pencil hardness, and good light fastness; a method for producing such a film; and a glass article having such a composition or film.

A further object of the present invention is to provide a compound for producing a composition capable of providing a film having long-wavelength ultraviolet range shielding properties, high pencil hardness, and good light fastness; and a method for producing such a compound.

A still further object of the present invention is to provide a high purity composition which is capable of accelerating a reaction rate and suppressing the formation of insoluble matters in the case of synthesizing a compound having a benzodithiol structure and a silane coupling group, which is used as a material of a film exhibiting long-wavelength ultraviolet range shielding properties, high pencil hardness and good light fastness and having a polysiloxane structure.

The present invention which is a specific means for achieving the foregoing objects and preferred aspects of the present invention are as follows.

[1] A composition, comprising:
a compound having a benzodithiol structure; and
a compound having an —O—Si—O— structure.

[2] The composition according to [1], in which the compound having a benzodithiol structure is a compound represented by General Formula (A) or General Formula (B):

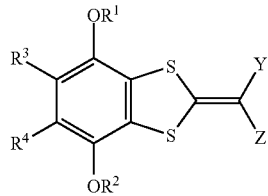

General Formula (A)

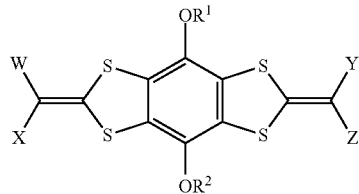

General Formula (B)

in General Formula (A) or General Formula (B), $R^1$ and $R^2$ each independently represent a hydrogen atom, an alkyl group, an aryl group, an acyl group, or a carbamoyl group, $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring; provided that $R^1$, $R^2$, $R^3$, $R^4$, W, X, Y, and Z may further have a substituent.

[3] The composition according to [2], in which, in General Formula (I) or General Formula (II), at least one of $R^1$ or $R^2$ is a hydrogen atom.

[4] The composition according to [1] or [2], in which the compound having a benzodithiol structure is a compound having a benzodithiol structure and a silane coupling group.

[5] The composition according to [4], in which the compound having a benzodithiol structure and a silane coupling group is a compound represented by General Formula (I) or General Formula (II):

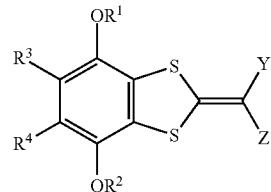

General Formula (I)

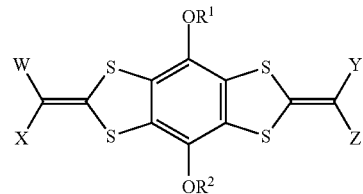

General Formula (II)

in General Formula (I) or General Formula (II), $R^1$ and $R^2$ each independently represent a hydrogen atom, an alkyl group, an aryl group, an acyl group, or a carbamoyl group, $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring; provided that $R^1$, $R^2$, $R^3$, $R^4$, W, X, Y, and Z may further have a substituent and at least one of R', $R^2$, $R^3$, $R^4$, W, X, Y, or Z contains a silane coupling group as a substituent.

[6] The composition according to [4] or [5], in which the silane coupling group is a trialkoxysilyl group, a dialkoxyalkylsilyl group, or an alkoxydialkylsilyl group.

[7] The composition according to any one of [4] to [6], in which, in General Formula (I) or General Formula (II), at least one of R' or $R^2$ is a hydrogen atom.

[8] The composition according to any one of [4] to [7], in which, in General Formula (I) or General Formula (II), at least one of R' or $R^2$ is a carbamoyl group or an alkyl group, and $R^3$ and $R^4$ are hydrogen atoms.

[9] The composition according to any one of [1] to [8], in which the compound having a —O—Si—O— structure is a hydrolyzable silicon compound.

[10] A film having a polysiloxane structure and formed from the composition according to any one of [1] to [9].

[11] A glass article, comprising:
a glass substrate; and
the composition according to any one of [1] to [9] or the film according to [10] positioned on at least a part of the glass substrate.

[12] A compound represented by General Formula (I) or General Formula (II):

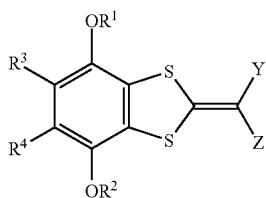

General Formula (I)

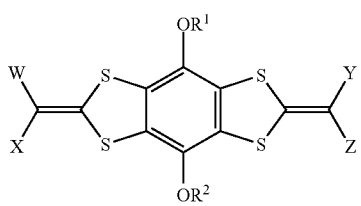

General Formula (II)

in General Formula (I) or General Formula (II), $R^1$ and $R^2$ each independently represent a hydrogen atom, an alkyl group, an aryl group, an acyl group, or a carbamoyl group, $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring; provided that $R^1$, $R^2$, $R^3$, $R^4$, W, X, Y, and Z may further have a substituent and at least one of $R^1$, $R^2$, $R^3$, $R^4$, X, Y, or Z has a silane coupling group as a substituent.

[13] The compound according to [12], in which, in General Formula (I) or General Formula (II), at least one of $R^1$ or $R^2$ is a group having a silane coupling group as a substituent, and $R^3$, $R^4$, W, X, Y, and Z do not have a silane coupling group as a substituent.

[14] A high purity composition, comprising:
90% by mass or more of a compound represented by General Formula (W) or General Formula (X) and having a moisture content of 2% by mass or less:

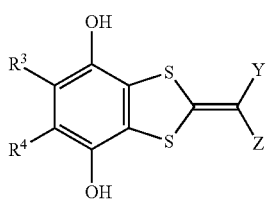

General Formula (W)

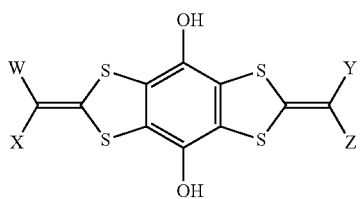

General Formula (X)

in General Formula (W) or General Formula (X), $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring.

[15] The high purity composition according to [14], which is for a material of a film having a polysiloxane structure.

[16] The high purity composition according to [14] or [15], which is for reaction with a compound represented by General Formula (Y):

A-L-M                General Formula (Y)

in General Formula (Y), A represents a substituent capable of reacting with a hydroxyl group, L represents a divalent group, and M represents a silane coupling group.

[17] A method for producing the compound according to [13], comprising:
reacting a compound represented by General Formula (W) or General Formula (X) with a compound represented by General Formula (Y):

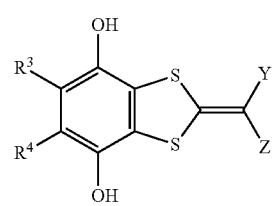

General Formula (W)

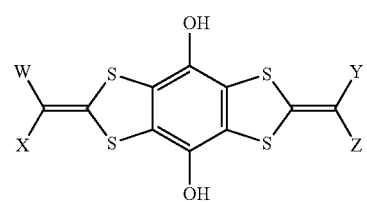

General Formula (X)

in General Formula (W) or General Formula (X), $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring;

A-L-M                General Formula (Y)

in General Formula (Y), A represents a substituent capable of reacting with a hydroxyl group, L represents a divalent group, and M represents a silane coupling group.

[18] The method for producing the compound according to [17], in which a high purity composition comprising a compound represented by General Formula (W) or General Formula (X) and having a moisture content of 2% by mass or less is used as the compound represented by General Formula (W) or General Formula (X):

[19] A method for producing the film according to [10], comprising:
reacting a compound having a benzodithiol structure with a compound having an —O—Si—O— structure in the presence of an acid catalyst or a base catalyst.

[20] The method for producing the film according to [19], further comprising:
reacting a compound represented by General Formula (A) or General Formula (B) with a hydrolyzable silicon compound in the presence of an acid catalyst:

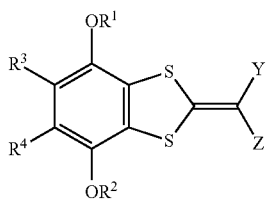

General Formula (A)

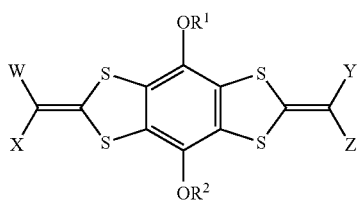

General Formula (B)

in General Formula (A) or General Formula (B), $R^1$ and $R^2$ each independently represent a hydrogen atom, an alkyl group, an aryl group, an acyl group, or a carbamoyl group, $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring; provided that $R^1$, $R^2$, $R^3$, $R^4$, W, X, Y, and Z may further have a substituent.

According to the present invention, it is possible to provide a composition capable of providing a film having long-wavelength ultraviolet range shielding properties, high pencil hardness, and good light fastness.

According to the present invention, it is possible to provide a film formed from a composition capable of providing a film having long-wavelength ultraviolet range shielding properties, high pencil hardness, and good light fastness; a method for producing such a film; and a glass article having such a composition or film.

According to the present invention, it is possible to provide a compound for producing a composition capable of providing a film having long-wavelength ultraviolet range shielding properties, high pencil hardness, and good light fastness; and a method for producing such a compound.

According to the present invention, it is possible to provide a high purity composition which is capable of accelerating a reaction rate and suppressing the formation of insoluble matters in the case of synthesizing a compound having a benzodithiol structure and a silane coupling group, which is used as a material of a film exhibiting long-wavelength ultraviolet range shielding properties, high pencil hardness and good light fastness and having a polysiloxane structure.

DESCRIPTION OF THE PREFERRED EMBODIMENTS

Figure 1:
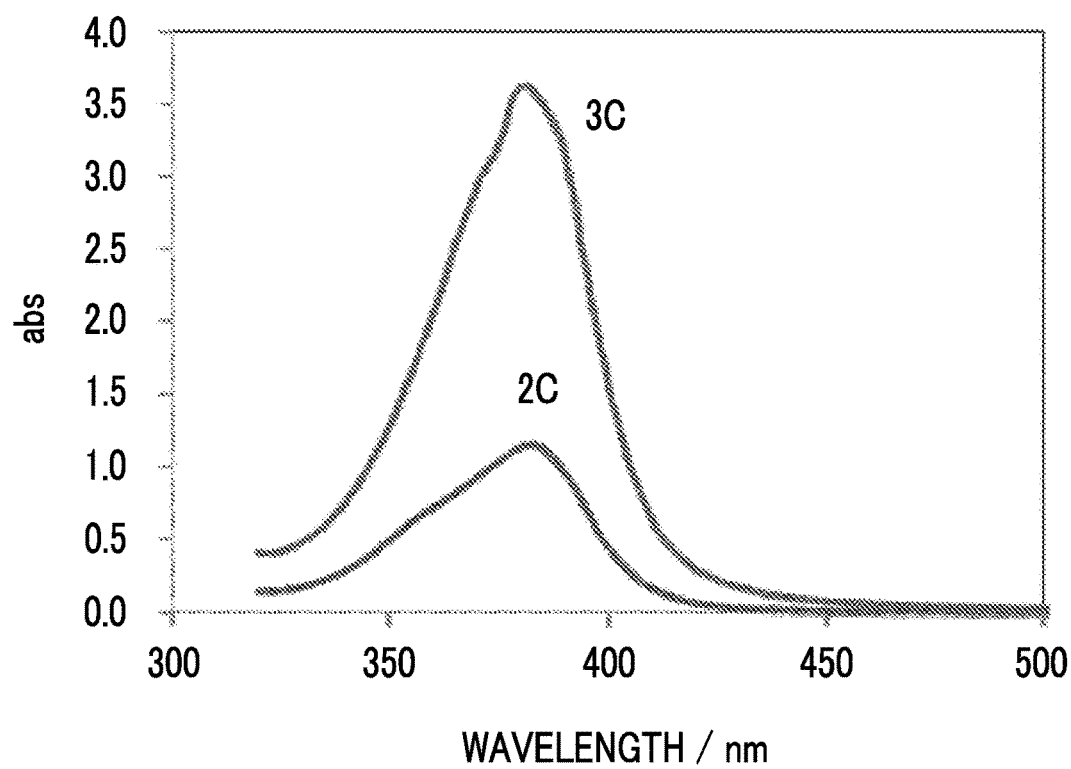
FIG. 1 shows absorption spectra of a sol-gel film (2C) which is a film of Example 1 and a sol-gel film (3C) which is a film of Example 2.

Hereinafter, the present invention will be described in detail. The description of the constituent features described below may be made based on representative embodiments of the present invention, but the present invention is not limited to such embodiments. In the present specification, the numerical range expressed using "to" means a range including numerical values described before and after "to" as a lower limit value and an upper limit value, respectively.

In the present specification, in the case where there are a plurality of substituents, linking groups, or the like (hereinafter, referred to as substituents or the like) indicated by specific symbols, or in the case where a plurality of substituents or the like are defined simultaneously or alternatively, the respective substituents or the like may be the same as or different from each other. Further, even in the case of being not specifically described, a plurality of substituents or the like may be linked to each other or may be condensed to form a ring in the case where they are adjacent to each other.

In the present specification, the term "compound (including resin)" includes not only the compound itself but also a salt thereof and an ion thereof, and is intended to include a derivative in which a predetermined part of the compound is changed within a range exhibiting a desired effect.

The term "substituent (the same applies also to the linking group)" in the present specification may have any substituent at that group within a range exhibiting a desired effect. This also applies to a compound that does not specify substituted or unsubstituted.

[Composition]

The composition of the present invention includes a compound having a benzodithiol structure and a compound having an —O—Si—O— structure. More specifically, the composition of the present invention can be used for forming a sol-gel film having a polysiloxane structure by including a compound having a benzodithiol structure and a compound having an —O—Si—O— structure.

With the above configuration, the composition of the present invention can provide a film having long-wavelength ultraviolet range shielding properties, high pencil hardness and good light fastness. By introducing an ultraviolet absorber with high fastness into a sol-gel film to form a composition with high pencil hardness and good light fastness, the composition can be used for applications such as windowpanes for building materials and windowpanes for automobiles, in particular, for high-performance glass for protection from sunburn.

Further, in the case where a conventionally known ultraviolet absorber having absorption of short wavelengths is introduced into a sol-gel film, the effect of protection from sunburn is insufficient.

Hereinafter, preferred aspects of the present invention will be described in detail.

<Compound Having Benzodithiol Structure, Compound of Present Invention>

(Structure of Compound Having Benzodithiol Structure)

The compound having a benzodithiol structure is preferably a compound represented by General Formula (A) or (B).

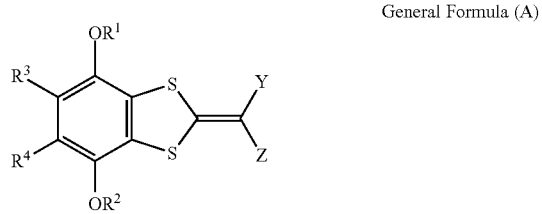

General Formula (A)

-continued

General Formula (B)

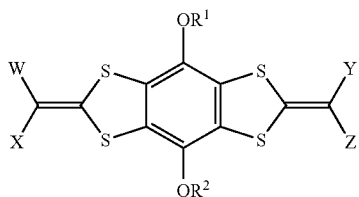

General Formula (II)

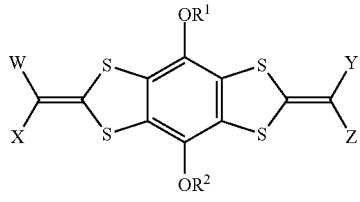

In General Formula (A) or General Formula (B), $R^1$ and $R^2$ each independently represent a hydrogen atom, an alkyl group, an aryl group, an acyl group, or a carbamoyl group, $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring; provided that $R^1$, $R^2$, $R^3$, $R^4$, W, X, Y, and Z may further have a substituent.

In General Formula (A) or General Formula (B), at least one of R' or $R^2$ is preferably a hydrogen atom.

It is also preferred that the compound represented by General Formula (A) or General Formula (B) is a compound having a benzodithiol structure and a silane coupling group, which will be described hereinafter;

a compound represented by General Formula (W) or (X), which will be described hereinafter; or other compounds having a benzodithiol structure, which will be described hereinafter.

A preferred structure of the compound represented by General Formula (A) or General Formula (B) will be described in the above order.

—Compound Having Benzodithiol Structure and Silane Coupling Group—

First, a case where the compound having a benzodithiol structure is a compound having a benzodithiol structure and a silane coupling group will be described.

Since the compound having a benzodithiol structure is a benzodithiol compound into which a silane coupling group is introduced which is a preferred aspect of the present invention, it is possible to produce a sol-gel film with high pencil hardness without bleed out (exudation of the compound from the film).

Specifically, in the present invention, it is preferred that the compound having a benzodithiol structure and a silane coupling group is a compound represented by General Formula (I) or General Formula (II).

General Formula (I)

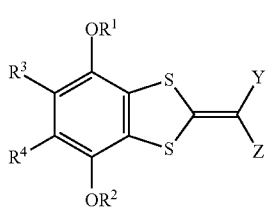

In General Formula (I) or General Formula (II), $R^1$ and $R^2$ each independently represent a hydrogen atom, an alkyl group, an aryl group, an acyl group, or a carbamoyl group, $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring; provided that $R^1$, $R^2$, $R^3$, $R^4$, W, X, Y, and Z may further have a substituent and at least one of $R^1$, $R^2$, $R^3$, $R^4$, W, X, Y, or Z has a silane coupling group as a substituent.

First, preferred aspects of the compound represented by General Formula (I) or General Formula (II) will be described.

In General Formula (I) or General Formula (II), $R^1$ and $R^2$ each independently represent a hydrogen atom, an alkyl group, an aryl group, an acyl group, or a carbamoyl group.

The alkyl group is preferably a linear, branched or cyclic alkyl group, and the number of carbon atoms thereof is preferably 1 to 30. The alkyl group is more preferably a substituent selected from the group consisting of a methyl group, an ethyl group, an n-propyl group, an isopropyl group, a tert-butyl group, an n-octyl group, an eicosyl group, a 2-chloroethyl group, a 2-cyanoethyl group, a benzyl group, a 2-ethylhexyl group, a vinyl group, an allyl group, a prenyl group, a geranyl group, an oleyl group, a propargyl group, a cyclohexyl group, a cyclopentyl group, a 2-hydroxyethyl group, a 2-hydroxypropyl group, a 7-trimethoxysilyl-4-oxa-2-hydroxyheptyl group, a 7-triethoxysilyl-4-oxa-2-hydroxyheptyl group, a 2-(3-trimethoxysilylpropylaminocarbonyloxy)ethyl group, a 2-(3-triethoxysilylpropylaminocarbonyloxy)ethyl group, or a 3-trimethoxysilylpropyl group. The alkyl group is particularly preferably an alkyl group having 1 to 15 carbon atoms and more particularly preferably a methyl group, an ethyl group, a 2-ethylhexyl group, a 2-hydroxyethyl group, a 7-trimethoxysilyl-4-oxa-2-hydroxyheptyl group, a 7-triethoxysilyl-4-oxa-2-hydroxyheptyl group, a 2-(3-trimethoxysilylaminocarbonyloxy)ethyl group, or a 2-(3-triethoxysilylaminocarbonyloxy) ethyl group.

The aryl group is preferably a substituted or unsubstituted aryl group having 6 to 30 carbon atoms, and examples thereof include a phenyl group, a paratolyl group, a naphthyl group, a metachlorophenyl group, and an orthohexadecanoylaminophenyl group. The aryl group is more preferably an aryl group having 6 to 10 carbon atoms, and particularly preferably a phenyl group. The acyl group is preferably an acyl group having 2 to 30 carbon atoms, and examples thereof include an acetyl group, a pivaloyl group, a 2-ethylhexanoyl group, a stearoyl group, a benzoyl group, and a paramethoxyphenylcarbonyl group. The acyl group is more preferably an acyl group having 2 to 15 carbon atoms, and particularly preferably an acetyl group, a pivaloyl group, or a 2-ethylhexanoyl group.

The carbamoyl group is preferably a substituted or unsubstituted carbamoyl group having 1 to 30 carbon atoms, and examples thereof include an N,N-dimethylcarbamoyl group, an N,N-diethylcarbamoyl group, a morpholinocarbonyl group, an N,N-di-n-octylaminocarbonyl group, an N-n-octylcarbamoyl group, an N-(3-trimethoxysilylpropyl)carbamoyl group, and an N-(3-triethoxysilylpropyl)carbamoyl group. The carbamoyl group is more preferably a carbamoyl group having 1 to 15 carbon atoms, and particularly preferably an N,N-dimethylcarbamoyl group, an N,N-diethylcarbamoyl group, an N-(3-trimethoxysilylpropyl)carbamoyl group, or an N-(3-triethoxysilylpropyl)carbamoyl group.

The foregoing substituent may further have a silane coupling group as a substituent.

In the present invention, it is preferred that at least one of $R^1$ or $R^2$ in General Formula (I) or General Formula (II) is a hydrogen atom from the viewpoint of ease of film formation. On the other hand, in the present invention, it is preferred that at least one of $R^1$ or $R^2$ in General Formula (I) or General Formula (II) is a carbamoyl group or an alkyl group from the viewpoint of ease of film formation.

In the present invention, it is more preferred that at least one of $R^1$ or $R^2$ in General Formula (I) or General Formula (II) is a carbamoyl group or an alkyl group and at least one of $R^1$ or $R^2$ is a hydrogen atom, from the viewpoint of ease of film formation.

In General Formula (I) or General Formula (II), $R^3$ and $R^4$ each independently represent a hydrogen atom, a halogen atom, an alkyl group, an aryl group, an alkoxy group, or an aryloxy group.

Examples of the halogen atom include a fluorine atom, a chlorine atom, and a bromine atom.

The alkyl group is preferably an alkyl group having 1 to 30 carbon atoms and more preferably a methyl group, an ethyl group, an n-propyl group, an isopropyl group, a tert-butyl group, an n-octyl group, a 2-cyanoethyl group, a benzyl group, a 2-ethylhexyl group, a vinyl group, an allyl group, a prenyl group, a geranyl group, an oleyl group, a propargyl group, a cyclohexyl group, a cyclopentyl group, a 2-hydroxyethyl group, or a 2-hydroxypropyl group.

The aryl group is preferably a substituted or unsubstituted aryl group having 6 to 30 carbon atoms and more preferably a phenyl group, a paratolyl group, or a naphthyl group The alkoxy group is preferably an alkoxyl group having 1 to 30 carbon atoms and more preferably a methoxy group or an ethoxy group.

The aryloxy group is preferably a substituted or unsubstituted aryloxy group having 6 to 30 carbon atoms. More preferred examples of the aryloxy group include a phenoxy group, a 2-methylphenoxy group, a 4-tert-butylphenoxy group, a 3-nitrophenoxy group, and a 2-tetradecanoylaminophenoxy group.

$R^3$ and $R^4$ are each particularly preferably a hydrogen atom, a fluorine atom, a chlorine atom, or a methyl group, and more particularly preferably a hydrogen atom.

In the foregoing substituents, the substituent capable of having a further substituent may have a silane coupling group as a further substituent.

The combination of $R^1$ and $R^2$ with $R^3$ and $R^4$ is not particularly limited. In the present invention, in General Formula (I) or General Formula (II), at least one of $R^1$ or $R^2$ is a carbamoyl group or an alkyl group, and $R^3$ and $R^4$ are each preferably a hydrogen atom.

In General Formula (I) or General Formula (II), W, X, Y, and Z each independently represent an electron withdrawing group. W and X may be bonded to each other to form a ring, and Y and Z may be bonded to each other to form a ring.

The electron withdrawing group represents a substituent having a positive Hammett's substituent constant σp value. Examples thereof include a cyano group, an acyl group, an alkoxycarbonyl group, an aryloxycarbonyl group, a carbamoyl group, a sulfonyl group, and a sulfamoyl group. The electron withdrawing group is preferably a cyano group or a carbamoyl group, and more preferably a carbamoyl group.

The acyl group is preferably an acetyl group, a propionyl group, a pivaloyl group, a benzoyl group, or a 4-methoxybenzoyl group. The alkoxycarbonyl group is preferably a methoxycarbonyl group, an ethoxycarbonyl group, a 2-hydroxyethoxycarbonyl group, a 2-(3-trimethoxysilylpropylaminocarbonyloxy)ethoxycarbonyl group, a 2-(3-triethoxysilylpropylaminocarbonyloxy)ethoxycarbonyl group, or a 2-ethylhexyloxycarbonyl group. The aryloxycarbonyl group is preferably a phenoxycarbonyl group or a 4-methoxyphenoxycarbonyl group. The carbamoyl group is preferably an unsubstituted carbamoyl group, an N,N-dimethylcarbamoyl group, an N,N-diethylcarbamoyl group, a morpholinocarbonyl group, an N,N-di-n-octylaminocarbonyl group, or an N-n-octylcarbamoyl group. The sulfonyl group is preferably a methanesulfonyl group, an ethanesulfonyl group, an octanesulfonyl group, or a benzenesulfonyl group. The sulfamoyl group is preferably an unsubstituted sulfamoyl group or an N,N-dimethylsulfamoyl group.

The ring formed by bonding W and X to each other and the ring formed by bonding Y and Z to each other are preferably a 5- or 6-membered ring. Specific examples thereof include 5-pyrazolone, isoxalin-5-one, pyrazolidine-3,5-dione, barbituric acid, thiobarbituric acid, and dihydropyridine-2,6-dione. These rings may further have a substituent.

In the foregoing substituents, the substituent capable of having a further substituent may have a silane coupling group as a further substituent.

$R^1$, $R^2$, $R^3$, $R^4$, W, X, Y, and Z in General Formula (I) or General Formula (II) may further have a substituent, and at least one of $R^1$, $R^2$, $R^3$, $R^4$, W, X, Y, or Z contains a silane coupling group as a substituent.

The silane coupling group represents a silyl group-substituted group having at least one functional group capable of imparting silanol by hydrolysis.

In the present invention, the silane coupling group is preferably a trialkoxysilyl group, a dialkoxyalkylsilyl group, or an alkoxydialkylsilyl group, and from the viewpoint of silanol formation rate, the silane coupling group is more preferably a trialkoxysilyl group or a dialkoxyalkylsilyl group.

The foregoing compound represented by General Formula (I) or General Formula (II) is a novel compound and is a compound of the present invention.

The compound of the present invention is preferably a compound in which, in General Formula (I) or General Formula (II), at least one of $R^1$ or $R^2$ is a group having a silane coupling group as a substituent, and $R^3$, $R^4$, W, X, Y, and Z (which may have a substituent) do not have a silane coupling group as a substituent.

Specific examples of the compound having a benzodithiol structure and a silane coupling group are listed below. However, the present invention is not limited to the following specific examples. Regioisomers of the following compounds are also preferred.

First, examples of the compound represented by General Formula (I) are as follows.
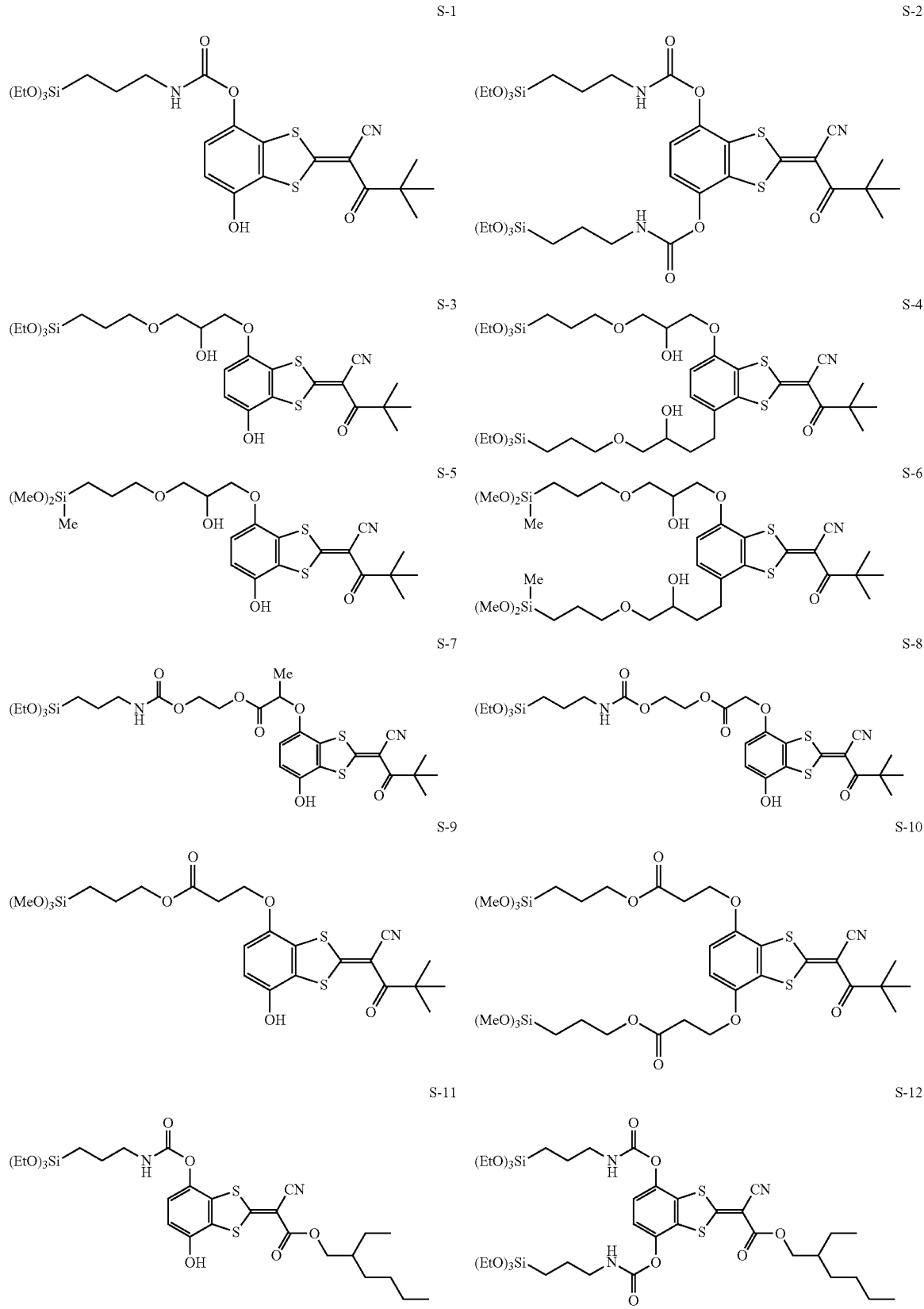

-continued
S-13
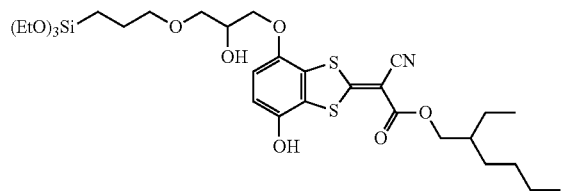
S-14
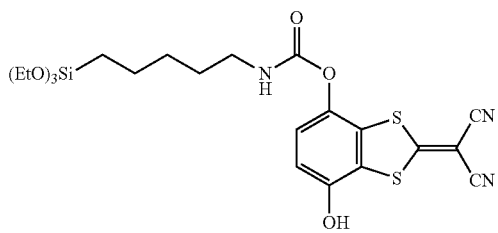
S-15
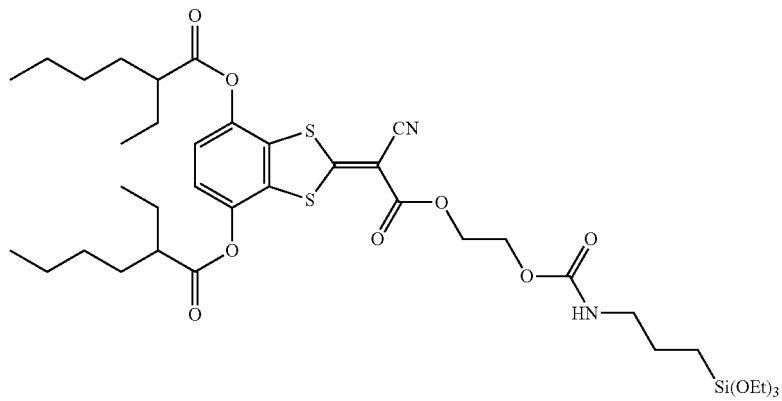
S-16
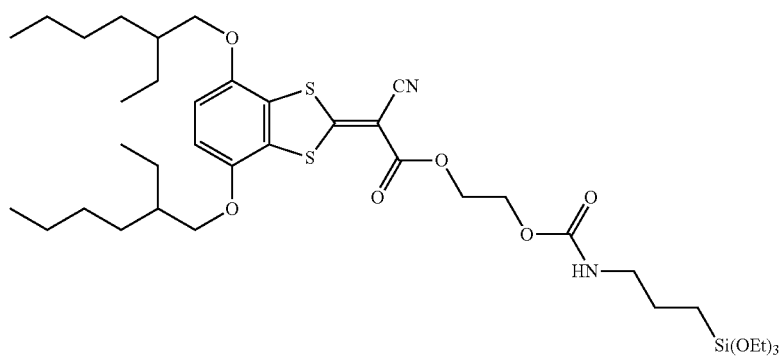
S-17
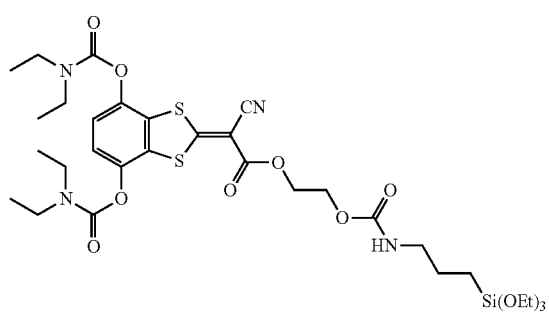
S-18
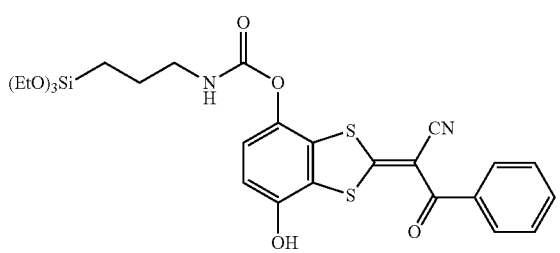
S-19
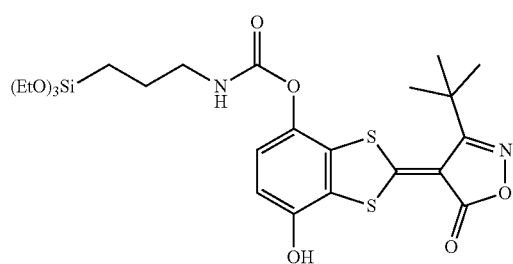
S-20
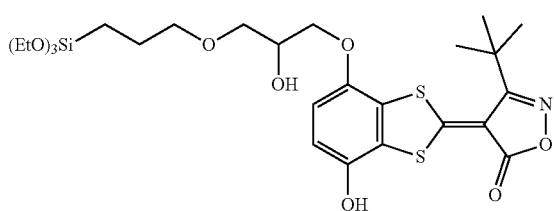

-continued
S-21
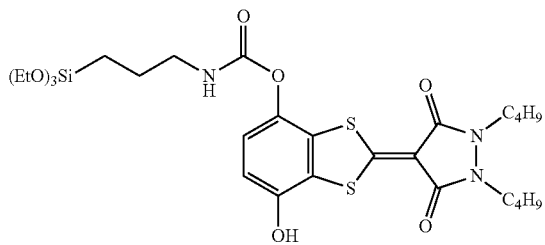
S-22
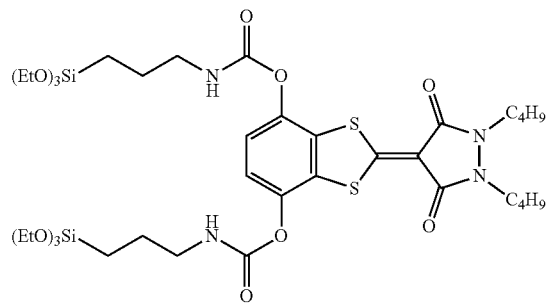
S-23
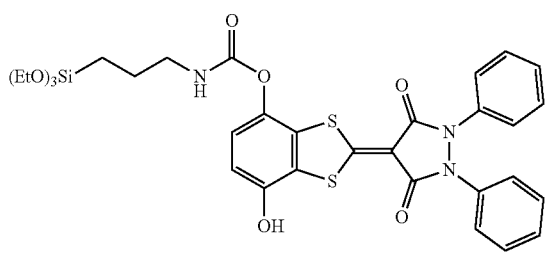
S-24
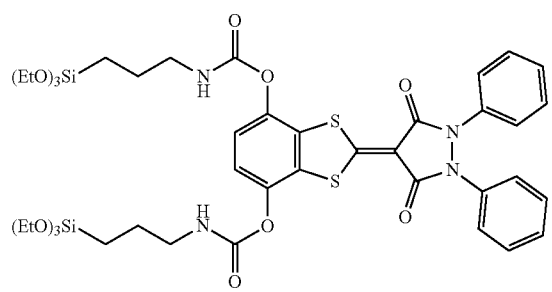
S-25
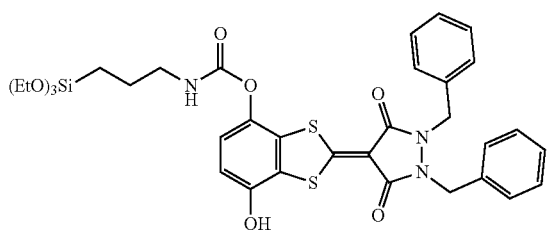
S-26
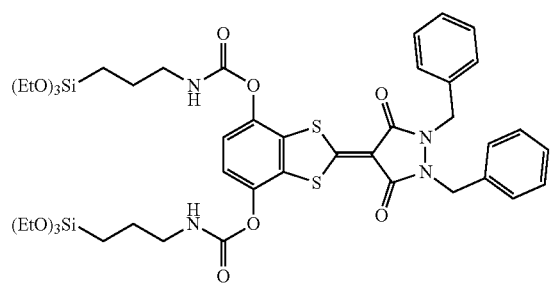
S-27
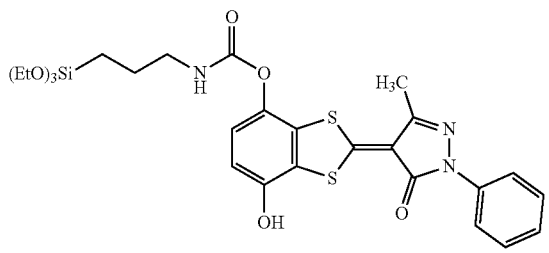
S-28
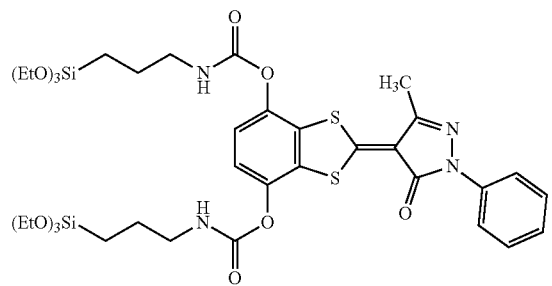
S-29
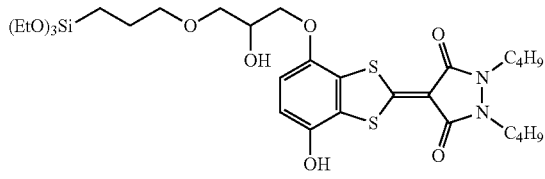
S-30
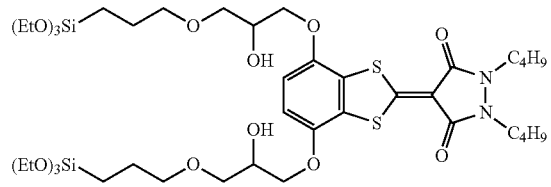

-continued
S-31
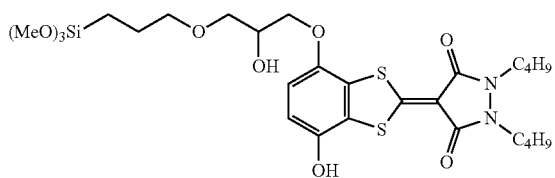
S-32
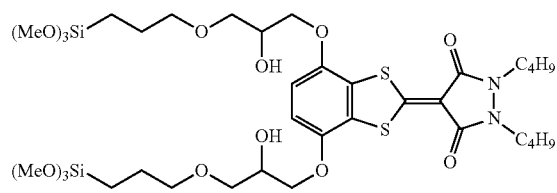
S-33
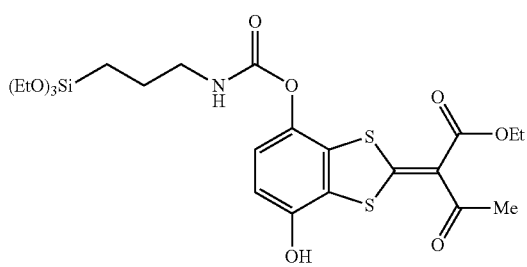
S-34
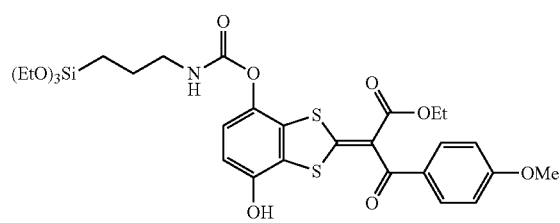
S-35
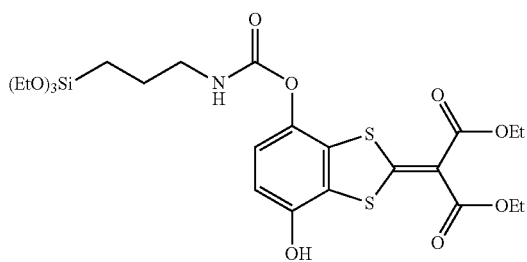
S-36
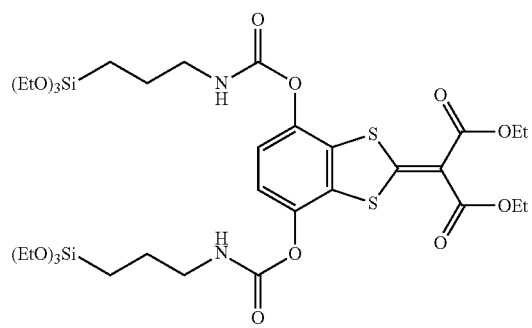
S-37
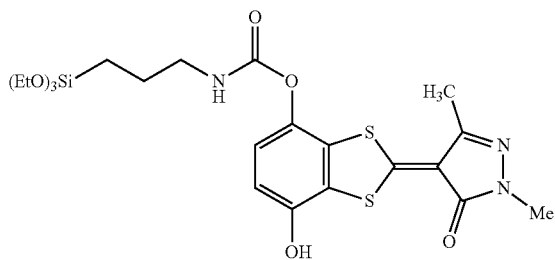
S-38
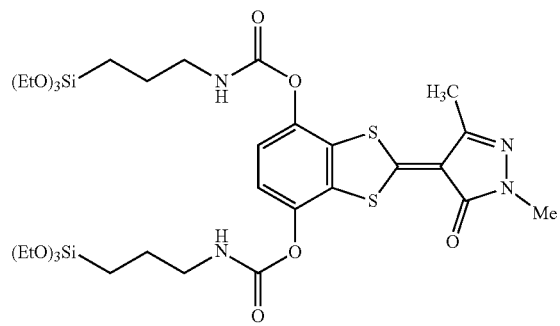
S-39
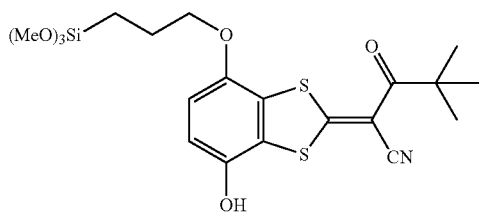
S-40
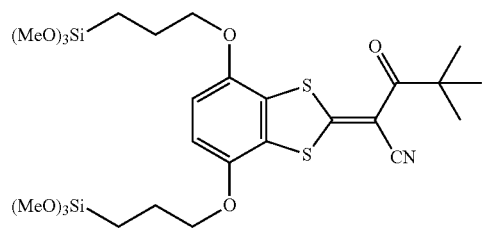

-continued
S-41
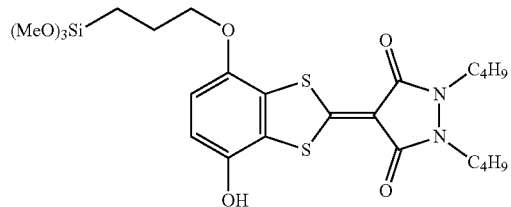
S-42
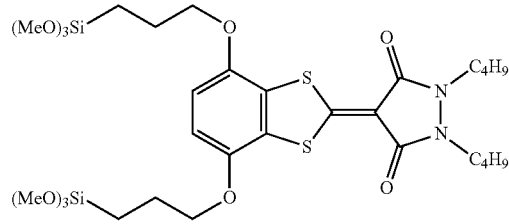
S-43
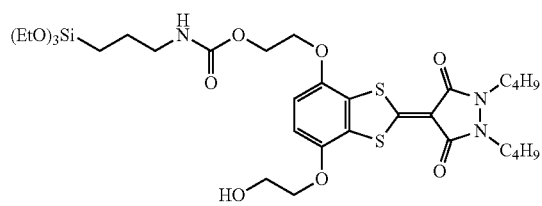
S-44
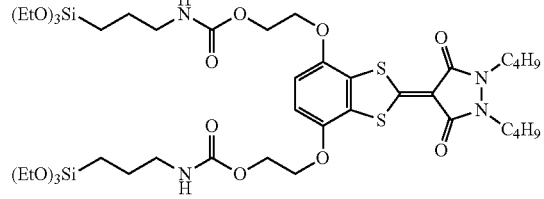
S-45
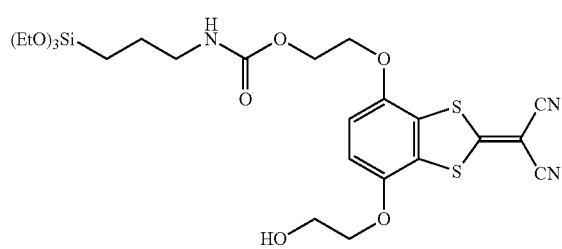
S-46
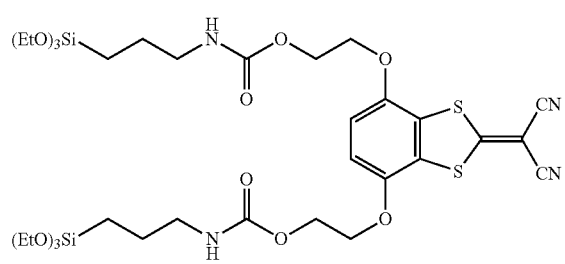
S-47
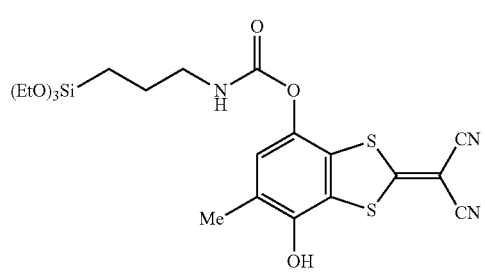
S-48
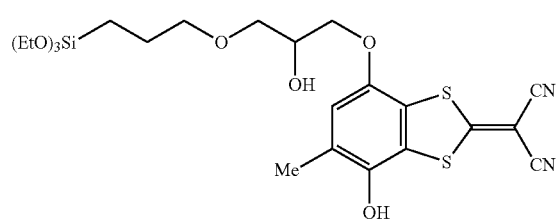
S-49
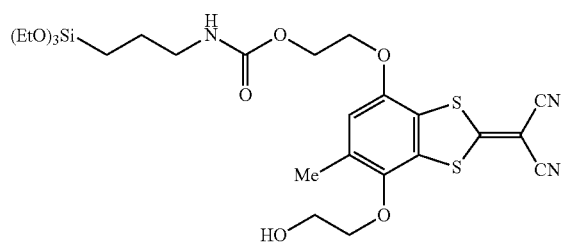
S-50
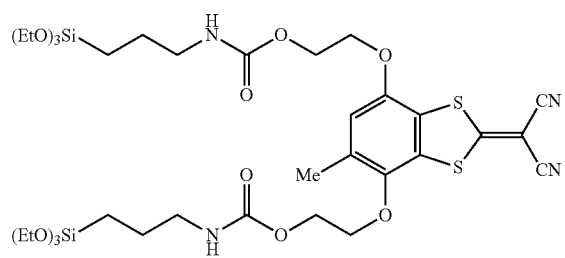
S-51
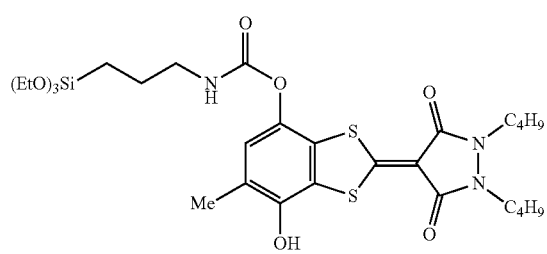
S-52
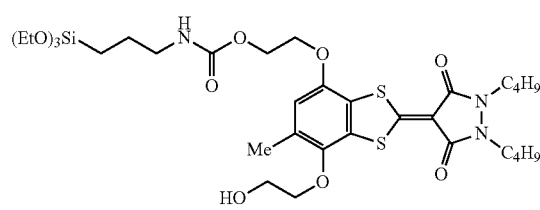

-continued
S-53
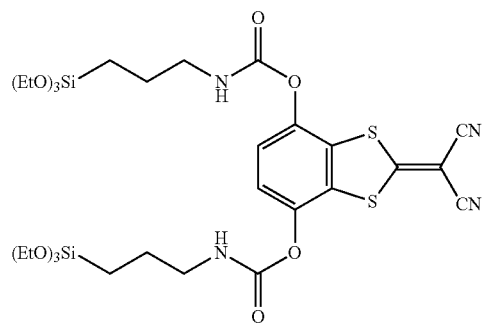
S-54
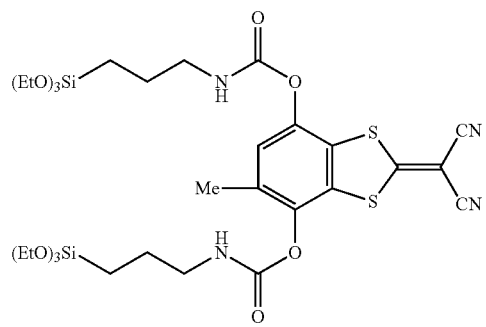
S-55
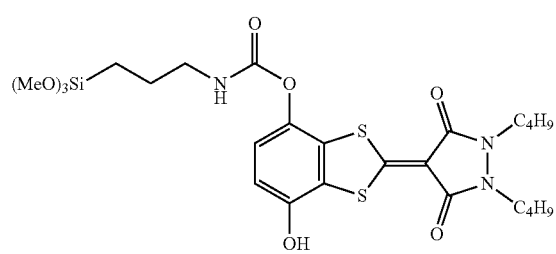
S-56
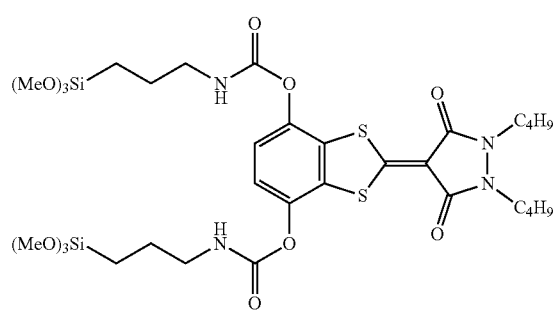
S-57
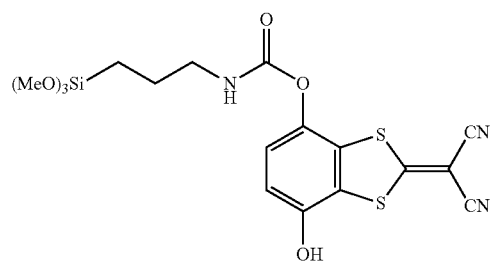
S-58
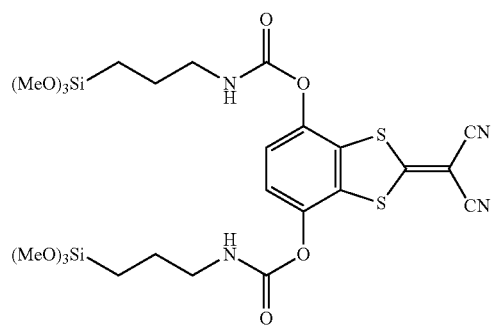
S-59
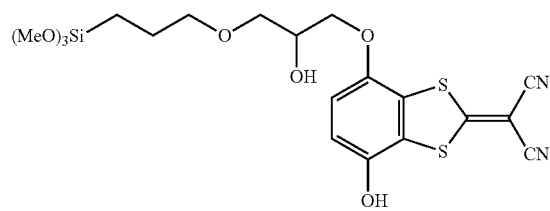
S-60
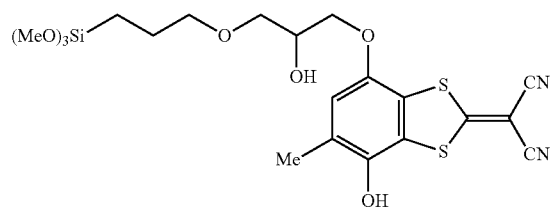

Next, examples of the compound represented by General Formula (II) are as follows.
S-61
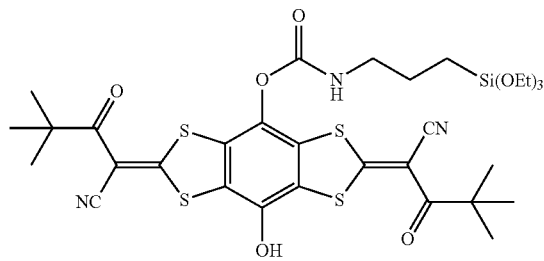
S-62
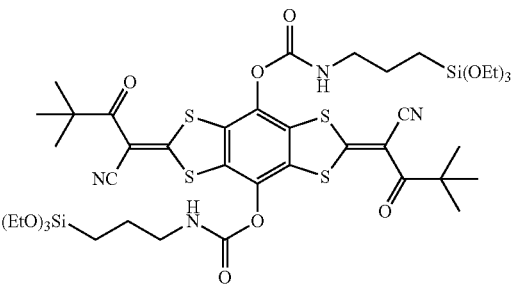
S-63
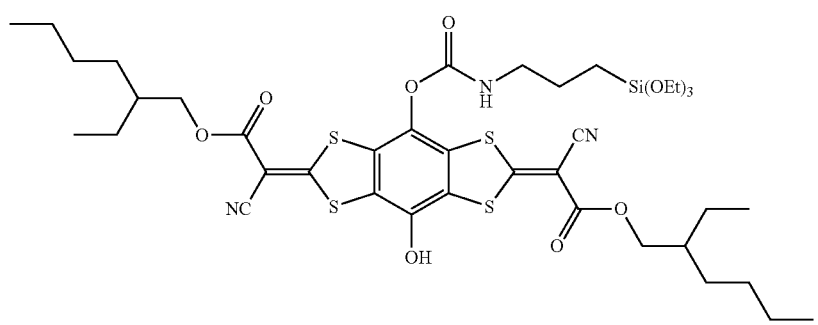
S-64
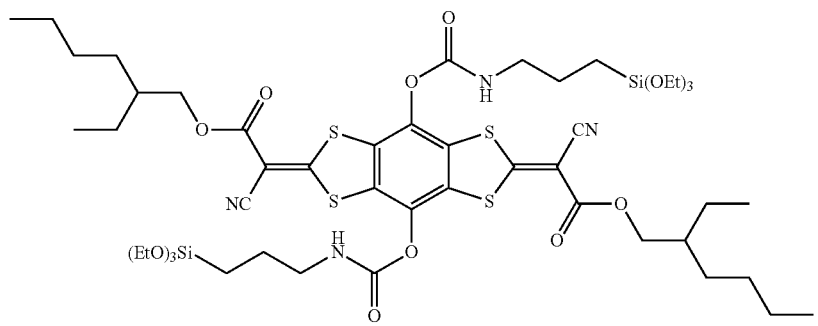
S-65
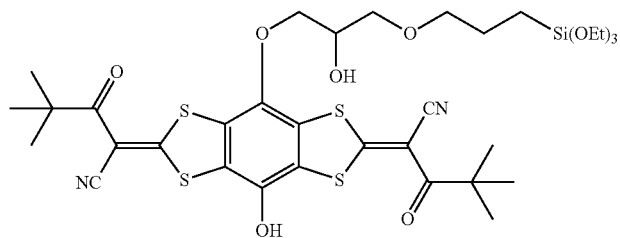
S-66
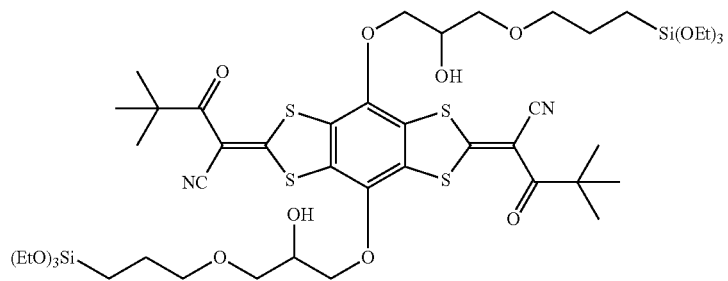

S-67
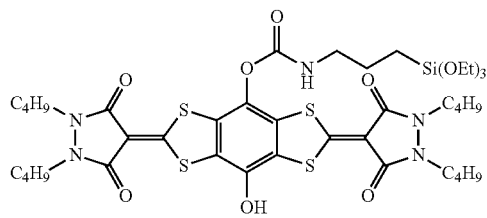

S-68
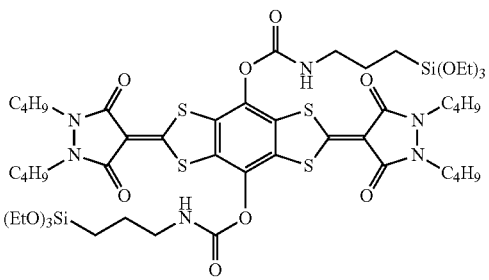

S-69
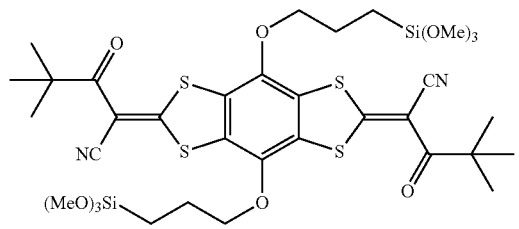

S-70
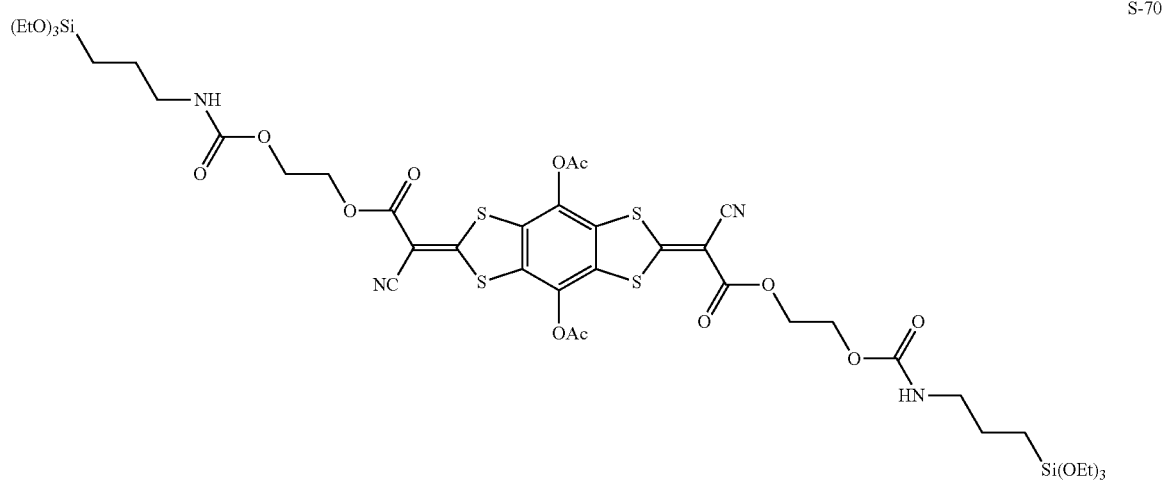

—Compound Represented by General Formula (W) or General Formula (X)—

In addition, the compound represented by General Formula (A) or (B) may be a compound represented by General Formula (W) or General Formula (X), and this case will be described. The compound represented by General Formula (W) or General Formula (X) is a compound in which $R^1$ and $R^2$ are both a hydrogen atom in the compound represented by General Formula (A) or General Formula (B).

General Formula (W)
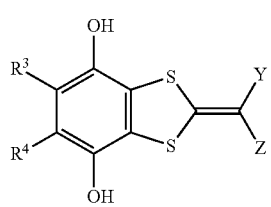

General Formula (X)
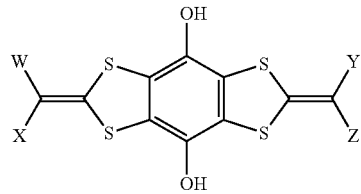

In General Formula (W) or General Formula (X), $R^1$ and $R^2$ each represent a hydrogen atom, and $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring; provided that $R^3$, $R^4$, W, X, Y, and Z may further have a substituent.

The compound represented by General Formula (W) or General Formula (X) may not have a silane coupling group.

That is, preferred aspects of $R^3$, $R^4$, W, X, Y, and Z in General Formula (W) or General Formula (X) are the same as the preferred aspects of $R^3$, $R^4$, W, X, Y, and Z in General Formula (I) or General Formula (II), but these compounds may not have a silane coupling group as a substituent. The compound represented by General Formula (W) or General Formula (X) preferably has no silane coupling group.

It is preferable to use the compound represented by General Formula (W) or General Formula (X) as a high purity composition in the case where a compound having a benzodithiol structure and a silane coupling group is synthesized, from the viewpoint of speeding up the reaction rate and inhibiting the formation of insoluble matters. The high purity composition of the present invention contains 90% by mass or more of a compound represented by General Formula (W) or General Formula (X) and has a moisture content of 2% by mass or less. The high purity composition preferably contains 90% by mass or more, more preferably 95% by mass or more, and particularly preferably 99% by mass or more of the compound represented by General Formula (W) or General Formula (X). The high purity composition preferably has a moisture content of 5% by mass or less, more preferably 2% by mass or less, and particularly preferably 1% by mass or less. The high purity composition may be a solid or a liquid and is preferably a solid. In the case where the high purity composition is a liquid, it is preferably a liquid in which a solvent other than water is used as a main solvent (a solvent contained in 50% by mass or more of the solvent). The high purity composition is preferably a solid and more preferably a powder.

Specific examples of the compound represented by General Formula (W) or General Formula (X) will be described later.

—Other Compounds Having Benzodithiol Structure—

The compound having a benzodithiol structure may be a compound having a benzodithiol structure other than the above-described compound having a benzodithiol structure and a silane coupling group or the above-described compound represented by General Formula (W) or General Formula (X).

Specific examples of other compounds having a benzodithiol structure are as follows.

T-1
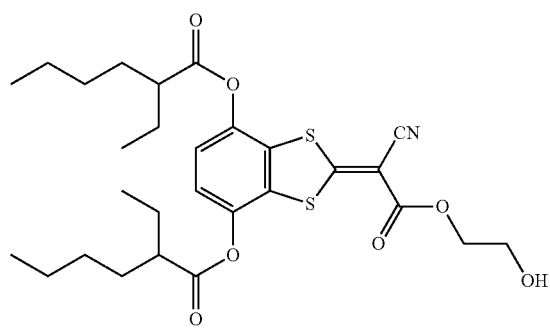

T-2
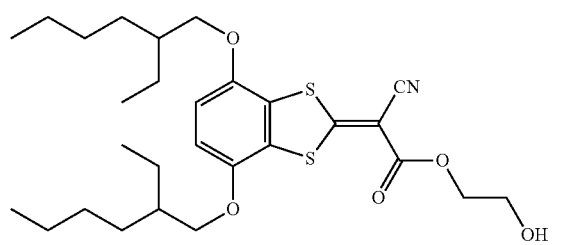

T-3
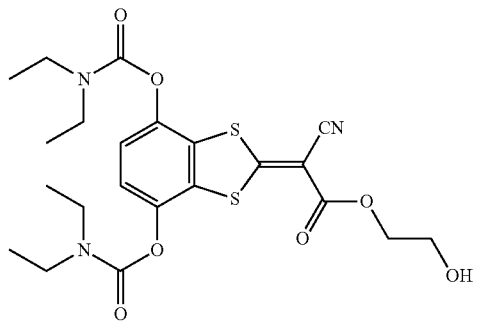

T-4
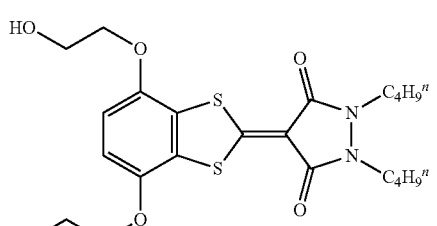

T-5
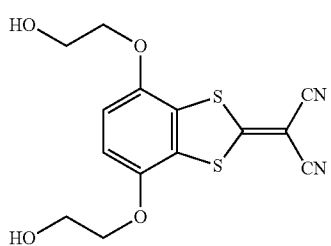

T-6
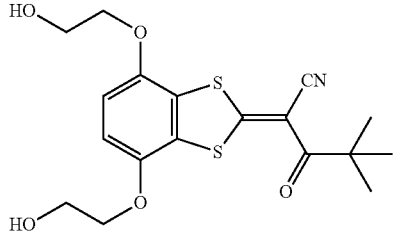

T-7
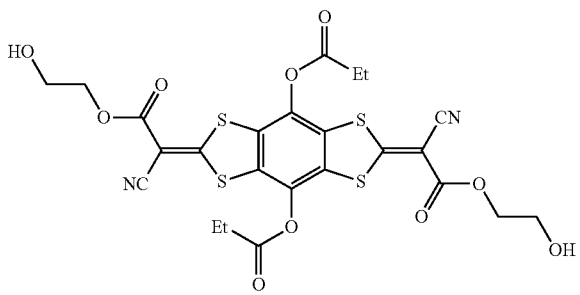

T-8
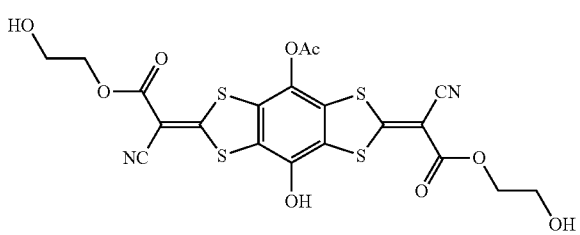

The concentration of the compound having a benzodithiol structure in the composition of the present invention is preferably 0.01 to 20% by mass, more preferably 0.01 to 10% by mass, and particularly preferably 0.1 to 10% by mass in the nonvolatile matter.

The compounds having a benzodithiol structure may be used alone or in combination of two or more thereof. In the case where two or more compounds are used in combination, it is preferred that the total concentration of the compounds having a benzodithiol structure in the composition of the present invention falls within the above-specified range.

(Method for Synthesizing Compound Having Benzodithiol Structure, and Method for Producing Compound of Present Invention)

The method for synthesizing the compound having a benzodithiol structure is not particularly limited, and a known method can be used.

Among the compounds having a benzodithiol structure, in particular, the compound represented by General Formula (I) or General Formula (II) is preferably produced by the following production method of the present invention. In particular, among the compounds of the present invention, the compound in which at least one of $R^1$ or $R^2$ in General Formula (I) or General Formula (II) is a group having a silane coupling group as a substituent, and $R^3$, $R^4$, W, X, Y, and Z do not have a silane coupling group as a substituent is more preferably produced by the following production method of the present invention.

In the method for producing the compound of the present invention, the compound represented by General Formula (W) or General Formula (X) is reacted with the compound represented by General Formula (Y).

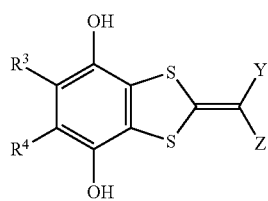

General Formula (W)

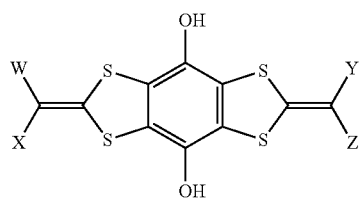

General Formula (X)

In General Formula (W) or General Formula (X), $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring;

A-L-M     General Formula (Y)

In General Formula (Y), A represents a substituent capable of reacting with a hydroxyl group, L represents a divalent group, and M represents a silane coupling group.

—Compound Represented by General Formula (W) or General Formula (X)—

Preferred aspects of the compound represented by General Formula (W) or General Formula (X) will be described.

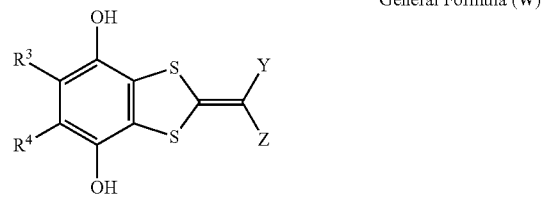

General Formula (W)

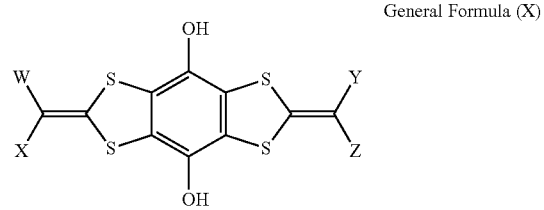

General Formula (X)

In General Formula (W) or General Formula (X), $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring.

Preferred aspects of $R^3$ and $R^4$ in General Formula (W) or General Formula (X) are the same as the preferred aspects of $R^3$ and $R^4$ in General Formula (I) or (II), except that $R^3$ and $R^4$ in General Formula (W) or General Formula (X) do not contain a silane coupling group as a substituent.

Preferred aspects of W, X, Y, and Z in General Formula (W) or General Formula (X) are the same as the preferred aspects of W, X, Y, and Z in General Formula (I) or (II), except that W, X, Y, and Z in General Formula (W) or General Formula (X) do not contain a silane coupling group as a substituent.

Specific examples of the compound represented by General Formula (W) or General Formula (X) are set forth below. However, the present invention is not limited to the following specific examples.

First, examples of the compound represented by General Formula (W) are as follows.

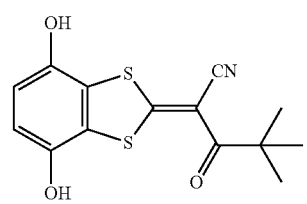

N-1

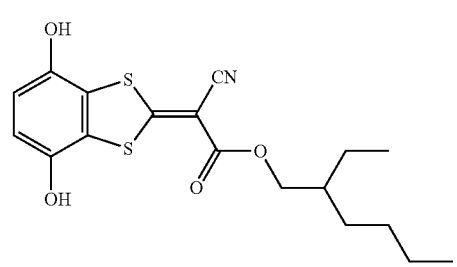

N-2

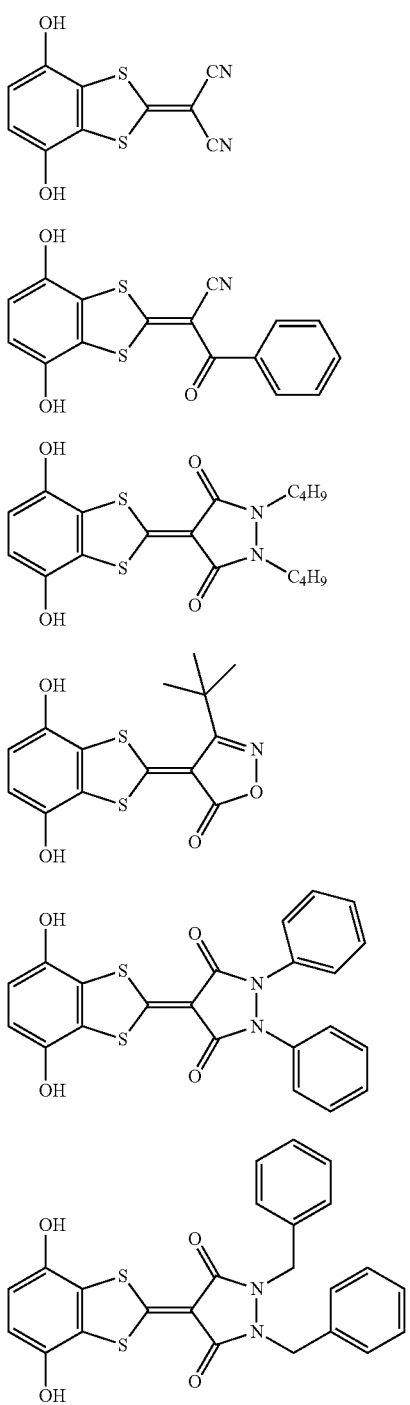
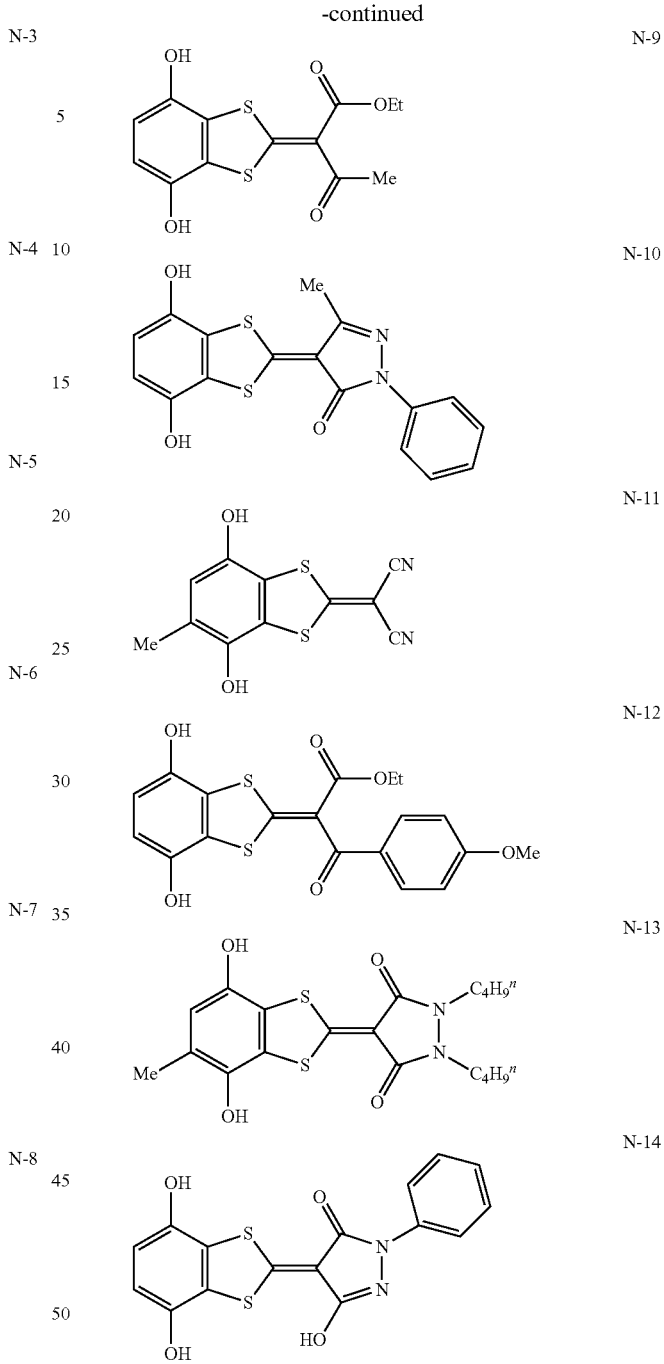
Next, examples of the compound represented by General Formula (X) are as follows.
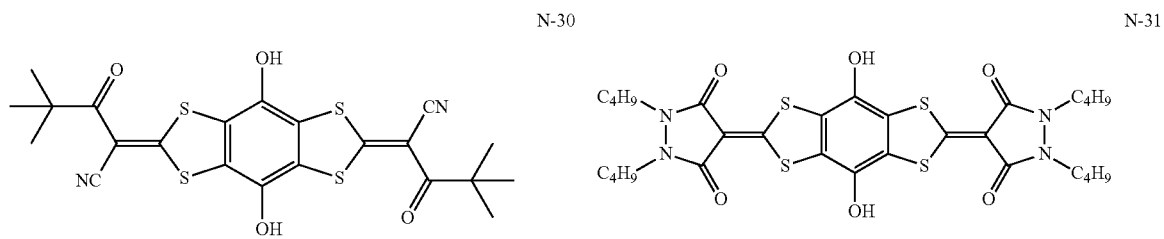

The compound of the present invention, that is, the compound represented by General Formula (I) or General Formula (II) may be obtained by reacting other compounds having a benzodithiol structure (specifically, compounds T-1 to T-8 and the like) with the compound represented by General Formula (Y), in addition to the above-mentioned method for producing the compound of the present invention.

—Compound Represented by General Formula (Y)—

Preferred aspects of the compound represented by General Formula (Y) will be described.

A-L-M        General Formula (Y)

In General Formula (Y), A represents a substituent capable of reacting with a hydroxyl group, L represents a divalent group, and M represents a silane coupling group.

In General Formula (Y), A represents a substituent capable of reacting with a hydroxyl group, examples of which include a group containing an epoxy group (for example, a glycidyl group) and an isocyanato group.

In General Formula (Y), L represents a divalent group, examples of which include an alkylene group (for example, an ethylene group, a propylene group, a 2-oxapentane-1,5-diyl group, or a 4-oxaheptane-1,7-diyl group), and an arylene group (for example, a phenylene group). These groups may further have a substituent.

In General Formula (Y), M represents a silane coupling group. A preferred aspect of the silane coupling group in General Formula (Y) is the same as the preferred aspect of the silane coupling group in General Formula (I) or (II).

Specific examples of the compound represented by General Formula (Y) are set forth below. However, the present invention is not limited to the following specific examples.

The compound represented by General Formula (Y) is preferably added in an amount of 50 to 1,000 mol %, more preferably 50 to 500 mol %, and particularly preferably 50 to 300 mol % with respect to the compound represented by General Formula (W) or General Formula (X).

—Catalyst—

In order to obtain the compound of the present invention represented by General Formula (I) or General Formula (II) from the compound represented by General Formula (W) or General Formula (X) and the compound represented by General Formula (Y), it is preferable to use a catalyst.

As the catalyst used for the reaction between the compound represented by General Formula (W) or General Formula (X) and the compound represented by General Formula (Y) having an epoxy group, a quaternary ammonium salt is preferable. Specific examples thereof include tetramethyl ammonium chloride, tetraethyl ammonium chloride, benzyl trimethyl ammonium chloride, benzyl triethyl ammonium chloride, benzyl triethyl ammonium bromide, benzyl triethyl ammonium iodide, tetrabutyl ammonium chloride, tetrabutyl ammonium bromide, and tetrabutyl ammonium iodide. Specific examples of the compound represented by General Formula (Y) used in this case include γ-glycidyloxypropyltrimethoxysilane, γ-glycidyloxypropyltriethoxysilane, γ-glycidyloxypropylmethyldimethoxysilane, γ-glycidyloxypropylmethyldiethoxysilane, and 2-(3,4-epoxycyclohexyl)ethyltrimethoxysilane. As the catalyst used for the reaction between the compound represented by General Formula (W) or General Formula (X) and the compound represented by General Formula (Y) having an isocyanato group, a tin- or bismuth-based catalyst is preferable. Specific examples thereof include dibutyltin, dioctyltin, dibutyltin dilaurate, di(2-ethylhexanoic acid) tin, and bismuth tris(2-ethylhexanoate). Specific examples of the compound represented by General Formula (Y) used in this case include 3-isocyanatopropyltrimethoxysilane and 3-isocyanatopropyltriethoxysilane.

—Other Production Conditions—

In addition, the preferred production conditions for obtaining the compound of the present invention represented by General Formula (I) or General Formula (II) from the compound represented by General Formula (W) or General Formula (X) and the compound represented by General Formula (Y) are as follows.

In this production, a reaction solvent may be used. Any solvent may be used as long as it does not react with the compound represented by General Formula (Y), and an ester-based solvent, an ether-based solvent, a hydrocarbon-based solvent, and a halogen-based solvent are preferable. Examples thereof include ethyl acetate, butyl acetate, tetrahydrofuran, methyl tert-butyl ether, methyl cyclopentyl ether, dioxane, toluene, and chlorobenzene. The boiling point of the solvent is preferably 200° C. or lower and particularly preferably 150° C. or lower.

The reaction temperature is preferably 0° C. to 200° C. and more preferably room temperature to 150° C.

In this production, it is preferable to remove water from the reaction system. For this purpose, it is preferable to dry and use the compound represented by General Formula (W) or General Formula (X) in advance. As a method for drying the composition containing the compound represented by General Formula (W) or General Formula (X), usual methods such as blast drying and drying under reduced pressure can be used. The moisture content of the composition containing the compound represented by General Formula (W) or General Formula (X) after drying is preferably 5% by mass or less, more preferably 2% by mass or less, and particularly preferably 1% by mass or less. In the method for producing the compound of the present invention, drying is preferably carried out until the moisture content of the composition containing the compound represented by General Formula (W) or General Formula (X) falls within the above-specified range. The drying temperature of the composition containing the compound represented by General Formula (W) or General Formula (X) is preferably 60° C. to 100° C., more preferably 70° C. to 100° C., and particularly preferably 75° C. to 100° C. In order to prevent water from entering the reaction system, it is preferable to carry out the reaction under dry air or dry nitrogen. The compound of the present invention represented by General Formula (I) or General Formula (II) can also be produced by using other conditions. For example, there is a method in which a compound having a mercapto group and a silane coupling group (specifically, 3-mercaptopropyltrimethoxysilane, 3-mercaptopropyltriethoxysilane, or the like) is reacted with a benzodithiol compound having an unsaturated bond (specifically, an allyl group or the like) in the presence of a radical generator (specifically, 2,2'-azobisisobutyronitrile, 2,2'-azobis(2-methylbutyronitrile), or the like). As this method, it is possible to use the method described in JP2006-63335A.

As another method, there is a method in which alkoxyhydrosilane (specifically, trimethoxysilane, triethoxysilane, dimethoxymethylsilane, diethoxymethylsilane, or the like) is reacted with a benzodithiol compound having an unsaturated bond (specifically, an allyl group, an allyloxy group, or the like) in the presence of a platinum catalyst (specifically, a 1,3-divinyl-1,1,3,3-tetramethyldisiloxane platinum complex or the like). As this method, it is possible to use the methods described in U.S. Pat. No. 5,391,795B, JP4912561B, and JP2004-075847A.

<Compound Having —O—Si—O— Structure>

The composition of the present invention includes a compound having an —O—Si—O— structure. It is also preferred that the compound having an —O—Si—O— structure is a compound capable of forming a sol-gel film having a polysiloxane structure by reacting with a compound having a benzodithiol structure.

Note that the compound having an —O—Si—O— structure may be a compound other than a hydrolyzable silicon compound. Known compounds can be used as the compound other than a hydrolyzable silicon compound.

In the composition of the present invention, it is preferred that the compound having an —O—Si—O— structure is a hydrolyzable silicon compound.

It is also preferred that the hydrolyzable silicon compound is a compound capable of forming a sol-gel film having a polysiloxane structure by reacting with a compound having a benzodithiol structure.

It is more preferred that the hydrolyzable silicon compound is a hydrolyzable alkoxysilane.

Examples of the hydrolyzable alkoxysilane used in the present invention include tetramethoxysilane, tetraethoxysilane, tetra-n-propoxysilane, tetra-i-propoxysilane, tetra-n-butoxysilane, methyltrimethoxysilane, methyltriethoxysilane, ethyltrimethoxysilane, ethyltriethoxysilane, n-propyltrimethoxysilane, n-propyltriethoxysilane, phenyltrimethoxysilane, phenyltriethoxysilane, γ-glycidyloxypropyltrimethoxysilane, γ-glycidyloxypropyltriethoxysilane, γ-glycidyloxypropylmethyldimethoxysilane, γ-glycidyloxypropylmethyldiethoxysilane, γ-methacryloyloxypropyltrimethoxysilane, γ-methacryloyloxypropyltriethoxysilane, γ-methacryloyloxypropylmethyldimethoxysilane, vinyltrimethoxysilane, vinyltriethoxysilane, 3,4-epoxycyclohexylethyltrimethoxysilane, 3,4-epoxycyclohexylethyltriethoxysilane, tris-(trimethoxysilylpropyl)isocyanurate, 4-trimethoxysilylstyrene, 3,3,3-trifluoropropyltrimethoxysilane, dimethyldimethoxysilane, dimethyldiethoxysilane, diethyldimethoxysilane, di ethyl diethoxysilane, di-n-propyldimethoxysilane, di-n-propyldiethoxysilane, diphenyldimethoxysilane, divinyldiethoxysilane, bis(triethoxysilylpropyl)tetrasulfide, 3-(trimethoxysilyl)propylisocyanate, and 3-(triethoxysilyl)propylisocyanate.

Particularly preferred are tetrafunctional and trifunctional alkoxysilanes.

These alkoxysilanes may be used alone or in combination of two or more thereof.

[Film]

The film of the present invention can be formed using the composition of the present invention.

The film of the present invention is a film having a polysiloxane structure and formed from the composition of the present invention and is preferably a sol-gel film formed by a sol-gel method, specifically a sol-gel film having a polysiloxane structure.

The film of the present invention preferably has an absorption maximum wavelength of 310 to 450 nm, more preferably 320 to 420 nm, and particularly preferably 350 to 400 nm.

In the film of the present invention, the long-wavelength ultraviolet range shielding property is preferably 0.1 or more, more preferably 0.5 or more, and particularly preferably 1.0 or more. The long-wavelength ultraviolet range shielding property refers to the absorbance at the absorption maximum wavelength.

The film of the present invention preferably has pencil hardness of 2 H or more, more preferably 3 H or more, and particularly preferably 4 H or more.

The film of the present invention preferably has light fastness (residual ratio) measured in Examples described later of 70% or more, more preferably 75% or more, and particularly preferably 80% or more.

The thickness of the film of the present invention is preferably 0.1 to 500 μm, more preferably 1 to 500 μm, particularly preferably 1 to 300 μm, more particularly preferably 20 to 300 μm, and still more particularly preferably 50 to 300 μm, from the viewpoint of long-wavelength ultraviolet range shielding properties.

[Method for Producing Film]

The method for producing a film of the present invention includes a step of reacting a compound having a benzodithiol structure and a compound having an —O—Si—O— structure in the presence of an acid catalyst or a base catalyst. It is preferable to carry out the reaction in the presence of an acid catalyst.

The method for producing a film of the present invention preferably includes a step of mixing a compound represented by General Formula (A) or General Formula (B) with a hydrolyzable silicon compound in the presence of an acid catalyst to cause a hydrolysis reaction.

In the method for producing a film of the present invention, it is more preferred that a compound represented by General Formula (A) or General Formula (B) is mixed with a hydrolyzable silicon compound in the presence of an acid catalyst to cause a hydrolysis reaction, the precursor constituted of a hydrolyzate of a hydrolyzable silanol compound is subjected to silanol condensation to effect a crosslinking reaction and a further heating or drying step is carried out to form a film.

The reaction of reacting the compound of the present invention with a compound having an —O—Si—O— structure (preferably, a hydrolyzable silicon compound) in the presence of an acid catalyst is a sol-gel reaction.

It is particularly preferred that the film of the present invention is produced by applying a coating liquid containing a compound represented by General Formula (A) or General Formula (B), at least one compound selected from hydrolyzable silicon compounds, an acid, and water onto a support. In this case, an organic solvent may be mixed in the coating liquid.

In the present invention, it is more particularly preferred that a film is obtained by subjecting a precursor constituted of a hydrolyzate of alkoxysilane to silanol condensation and curing the resulting condensate by a crosslinking reaction.

(Compound Having —O—Si—O— Structure)

The compound having an —O—Si—O— structure can be the same compound as the compound having an —O—Si—O— structure contained in the above-mentioned composition of the present invention, and the same applies to a preferred range thereof.

(Solvent)

The solvent used for a sol-gel reaction is not particularly limited as long as it dissolves a compound having a benzodithiol structure and a compound having an —O—Si—O— structure. The solvent is preferably alcohols, among which methanol, ethanol, 1-propanol, 2-propanol, 1-butanol, 2-butanol, 2-methyl-1-propanol, 1-methoxy-2-propanol, 2-ethoxyethanol, 2-butoxyethanol, polyethylene glycol monoalkyl ether, polypropylene glycol monoalkyl ether, ethylene glycol, propylene glycol, polyethylene glycol, polypropylene glycol, and glycerin are more preferable. Examples of other solvents that can be used include ethylene carbonate, N-methylpyrrolidone, dioxane, tetrahydrofuran, ethylene glycol dialkyl ether, propylene glycol dialkyl ether, polyethylene glycol dialkyl ether, polypropylene glycol dialkyl ether, acetonitrile, propionitrile, benzonitrile, carboxylic acid ester, phosphoric acid ester, phosphonic acid ester, dimethylsulfoxide, sulfolane, dimethylformamide, and dimethylacetamide. These solvents may be used alone or in combination of two or more thereof.

(Acid Catalyst and Base Catalyst)

As the acid catalyst used in the present invention, a common acid can be used. Specific examples thereof include hydrochloric acid, sulfuric acid, acetic acid, and propionic acid.

As the base catalyst used in the present invention, a common base can be used. Specific examples thereof include sodium hydroxide, potassium hydroxide, and triethylamine.

The reaction temperature of the sol-gel reaction can be selected depending on the reactivity of the starting compound and the type and amount of the selected acid or base used in the sol-gel reaction, in relation to the reaction rate. The reaction temperature of the sol-gel reaction is preferably −20° C. to 150° C., more preferably 0° C. to 80° C., and still more preferably 20° C. to 60° C.

(Support)

The support onto which the sol-gel reaction mixture is applied is not particularly limited, but preferred examples thereof include a glass substrate, a metal substrate, and a polymer film. Examples of the polymer film include cellulose-based polymer films such as triacetyl cellulose (TAC), ester-based polymer films such as polyethylene terephthalate (PET) and polyethylene naphthalate (PEN), fluorine-based polymer films such as polytrifluoroethylene (PTFE), and polyimide films.

A coating method may be a known method. For example, a curtain coating method, an extrusion coating method, a roll coating method, a spin coating method, a dip coating method, a bar coating method, a spray coating method, a slide coating method, or a printing coating method can be used.

(Other Ultraviolet Absorbers)

In the present invention, a compound having a benzodithiol structure and other ultraviolet absorbers may be used in combination. Examples of other ultraviolet absorbers include 2-(2-hydroxyphenyl)benzotriazoles, 2-(2-hydroxyphenyl)-4,6-diphenyl-1,3,5-triazines, and 2-hydroxybenzophenones.

Specific examples of the benzotriazole-based ultraviolet absorber include 2-[5-chloro(2H)-benzotriazol-2-yl]-4-methyl-6-(tert-butyl)phenol (commercially available TINUVIN TINUVIN 326 (trade name, manufactured by BASF Corporation) or the like), octyl 3-[3-tert-butyl-4-hydroxy-5-(5-chloro-2H-benzotriazol-2-yl)]phenylpropionate, 2-(2H-benzotriazol-2-yl)-4,6-di-tert-pentylphenol, 2-(2-hydroxy-5-methylphenyl)benzotriazole, 2-[2-hydroxy-3-(3,4,5,6-tetrahydrophthalimide-methyl)-5-methylphenyl]

benzotriazole, 2-(2-hydroxy-5-tert-octylphenyl) benzotriazole, 2-(2-hydroxy-5-tert-butylphenyl)-2H-benzotriazole, methyl 3-(3-(2H-benzotriazol-2-yl)-5-t-butyl-4-hydroxyphenyl)propionate, 2-(2H-benzotriazol-2-yl)-4,6-bis(1-methyl-1-phenylethyl)phenol, and 2-(2H-benzotriazol-2-yl)-6-(1-methyl-1-phenylethyl)-4-(1,1,3,3-tetramethylbutyl)phenol.

Specific examples of the triazine-based ultraviolet absorber include 2-[4-[(2-hydroxy-3-dodecyloxypropyl)oxy]-2-hydroxyphenyl]-4,6-bis(2,4-dimethylphenyl)-1,3,5-triazine, 2-[4-[(2-hydroxy-3-(2'-ethyphexypoxy]-2-hydroxyphenyl]-4,6-bis(2,4-dimethylphenyl)-1,3,5-triazine, 2,4-bis(2-hydroxy-4-butoxyphenyl)-6-(2,4-bis-butoxyphenyl)-1,3,5-triazine, 2-(2-hydroxy-4-[1-octylcarbonylethoxy]phenyl)-4,6-bis(4-phenylphenyl)-1,3,5-triazine, and TINUVIN 477 (trade name, manufactured by BASF Corporation).

Specific examples of the benzophenone-based ultraviolet absorber include 2,4-dihydroxybenzophenone, any of 2,2',3 (or 4,5,6)-trihydroxybenzophenone, 2,2',4,4'-tetrahydroxybenzophenone, 2,4-dihydroxy-2',4'-dimethoxybenzophenone, and 2-hydroxy-4-n-octoxybenzophenone.

[Glass Article]

The glass article of the present invention includes a glass substrate and a composition of the present invention or a film of the present invention positioned on at least a portion of the glass substrate.

Specific examples of the glass article include windowpanes for automobiles and windowpanes for building materials.

EXAMPLES

Hereinafter, the present invention will be described in more detail with reference to Examples and Comparative Examples (Note that Comparative Examples are not well-known techniques). The materials, amount of use, proportion, treatment content, treatment procedure, and the like shown in the following Examples can be appropriately changed without departing from the gist of the present invention. Therefore, the scope of the present invention should not be construed as being limited by the following specific examples.

Incidentally, "part" and "%" in the text are on a mass basis unless otherwise indicated.

The moisture content of the compound represented by General Formula (W) or General Formula (X) was measured by Karl Fischer coulometric titration using AQS-225320 and AQ-2250 (both manufactured by Hiranuma Sangyo Co., Ltd.)

<Synthesis of Exemplary Compound N-5 with Moisture Content of 0.8% by Mass>

19.7 g (0.06 mol) of 1-(4,7-dihydroxybenzo[1,3]dithiol-2-ylidene)piperidinium acetate and 60 mL of N-methylpyrrolidone were added to 14.0 g (0.066 mol) of 1,2-dibutylpyrazolidine-3,5-dione, and the mixture was stirred at 80° C. for 1 hour under nitrogen flow conditions. The obtained reaction liquid was then cooled, and 600 mL of diluted hydrochloric acid was added to the cooled reaction liquid and the precipitated solid (crude crystal) was collected by filtration. 40 mL of acetonitrile was added to the obtained crude crystal which was then stirred at room temperature. After stirring, the solid (crystal) was collected by filtration and dried at 80° C. under reduced pressure. 23.9 g of Exemplary Compound N-5 after drying was obtained. The obtained Exemplary Compound N-5 had a purity of 98.2% and a moisture content of 0.8% by mass.

<Synthesis of Exemplary Compound N-5 with Moisture Content of 5.8% by Mass>

19.7 g (0.06 mol) of 1-(4,7-dihydroxybenzo[1,3]dithiol-2-ylidene)piperidinium acetate and 60 mL of N-methylpyrrolidone were added to 14.0 g (0.066 mol) of 1,2-dibutylpyrazolidine-3,5-dione, and the mixture was stirred at 80° C. for 1 hour under nitrogen flow conditions. The obtained reaction liquid was then cooled, and 600 mL of diluted hydrochloric acid was added to the cooled reaction liquid and the precipitated solid (crude crystal) was collected by filtration. 40 mL of acetonitrile was added to the obtained crude crystal which was then stirred at room temperature. After stirring, the solid (crystal) was collected by filtration and blast-dried at 50° C. 24.0 g of Exemplary Compound N-5 after drying was obtained. The obtained Exemplary Compound N-5 had a purity of 93.2% and a moisture content of 5.8% by mass.

The other compounds represented by General Formula (W) or General Formula (X) were synthesized in the same manner as Exemplary Compound N-5, while controlling the moisture content.

<Synthesis of Exemplary Compound S-21 (Using High-Purity Exemplary Compound N-5)>

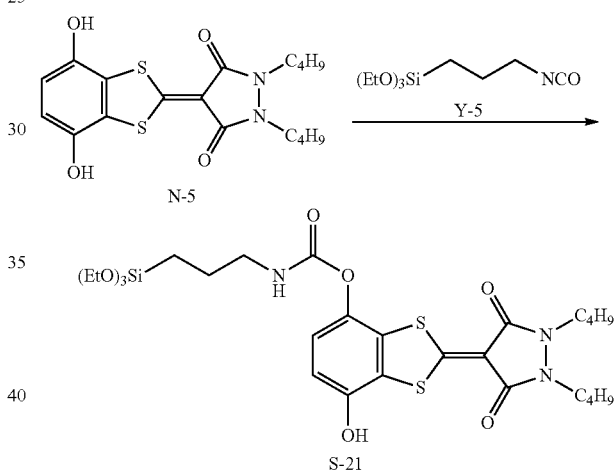

Under a nitrogen atmosphere, 1.57 g (moisture content: 0.8% by mass) of Exemplary Compound N-5 which is a compound represented by General Formula (W), 1.98 g of 3-triethoxysilylpropyl isocyanate (Y-5) which is a compound represented by General Formula (Y), and 6.3 mL of dry tetrahydrofuran were stirred, and one drop of dibutyltin dilaurate was added to this mixture. In the case where the mixture was refluxed with heating for 3 hours under a nitrogen atmosphere, TLC analysis was carried out to confirm that the reaction was almost completed, and the mixture was further refluxed with heating for 2 hours so that the mixture was refluxed with heating for a total of 5 hours. The reaction mixture was concentrated, and proton Nuclear Magnetic Resonance (NMR) was measured. As a result, the production of Exemplary Compound S-21, which is a compound having a benzodithiol structure, was confirmed. In addition, as a result of Thin-Layer Chromatography (TLC) analysis of the reaction mixture, the production of Exemplary Compound S-21 was supported (rate of flow (Rf) value of Exemplary Compound N-5: 0.17, Rf value of Exemplary Compound S-21: 0.42, TLC plate: TLC silica gel 60F254 manufactured by Merck Corporation, Deployment solvent: ethyl acetate/n-hexane=1/1 by volume).

$^1$H-NMR (CDCl$_3$) δ9.12 (br., 1H), 7.12 (d, 1H), 6.94 (d, 1H), 5.76 (br., 1H), 3.85 (q, 6H), 3.68 (t, 4H), 3.30 (t, 2H), 1.73 (m, 2H), 1.64 (m, 4H), 1.31 (m, 4H), 1.28 (t, 9H), 0.90 (t, 6H), 0.70 (t, 2H).

<Synthesis of Exemplary Compound S-21 (Using Low-Purity Example Compound N-5)>

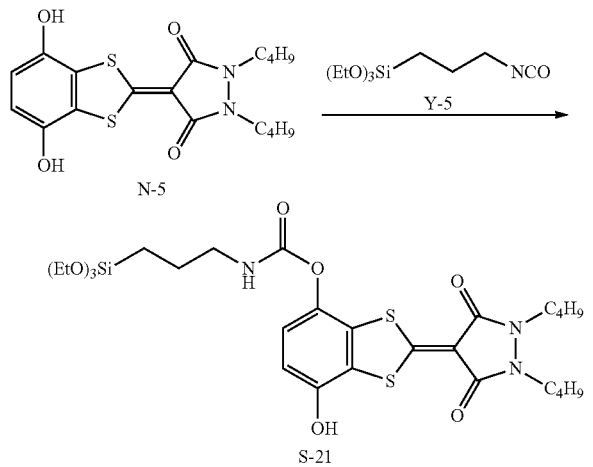

Under a nitrogen atmosphere, 1.57 g (moisture content: 5.8% by mass) of Exemplary Compound N-5 which is a compound represented by General Formula (W), 1.98 g of 3-triethoxysilylpropyl isocyanate (Y-5) which is a compound represented by General Formula (Y) and 6.3 mL of dry tetrahydrofuran were stirred, and one drop of dibutyltin dilaurate was added to this mixture. The mixture was refluxed with heating for 3 hours under a nitrogen atmosphere. Since the progress of the reaction was slow as compared with the time in the case where the high-purity Exemplary Compound N-5 was used and refluxed with heating for 3 hours, 1.98 g of 3-triethoxysilylpropyl isocyanate (Y-5) which is a compound represented by General Formula (Y) was added, and the mixture was further refluxed with heating for 3 hours. As a result of TLC analysis of the reaction mixture, the production of Exemplary Compound S-21 was confirmed.

By comparison with the case of using the low-purity Exemplary Compound N-5, it was found that, by using a high purity composition containing 90% by mass of the compound represented by General Formula (W) and having a moisture content of 2% by mass or less, the reaction rate in the reaction with the compound represented by General Formula (Y) having an isocyanato group can be accelerated. The reason for this is presumed to be that the decomposition of 3-triethoxysilylpropyl isocyanate (Y-5) due to water in the material could be suppressed.

<Synthesis of Exemplary Compound S-14 (Using High-Purity Exemplary Compound N-3)>

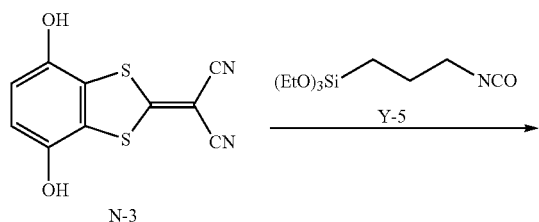

Under a nitrogen atmosphere, 1.00 g (moisture content: 0.1% by mass) of Exemplary Compound N-3 which is a compound represented by General Formula (W), 1.00 g of 3-triethoxysilylpropyl isocyanate (Y-5) which is a compound represented by General Formula (Y) and 4.0 mL of dry tetrahydrofuran were stirred, and one drop of dibutyltin dilaurate was added to this mixture. The mixture was reacted at 60° C. for 2 hours under a nitrogen atmosphere. The reaction mixture was concentrated, and the proton NMR was measured. As a result, the production of Exemplary Compound S-14, which is a compound having a benzodithiol structure, was confirmed. In addition, as a result of TLC analysis of the reaction mixture, the production of Exemplary Compound S-14 was supported, and it was confirmed that the reaction was completed in 2 hours (Rf value of Exemplary Compound N-3: 0.20, Rf value of Exemplary Compound S-14: 0.37, TLC plate: TLC silica gel 60F254 manufactured by Merck Corporation, Deployment solvent: ethyl acetate/n-hexane=1/1 by volume).

$^1$H-NMR (CDCl$_3$) δ8.63 (br., 1H), 7.05 (d, 1H), 6.67 (d, 1H), 5.90 (t, 1H), 3.89 (q, 6H), 3.32 (dt, 2H), 1.74 (m, 2H), 1.23 (t, 9H), 0.70 (t, 2H)

<Synthesis of Exemplary Compound S-14 (Using Low-Purity Exemplary Compound N-3)>

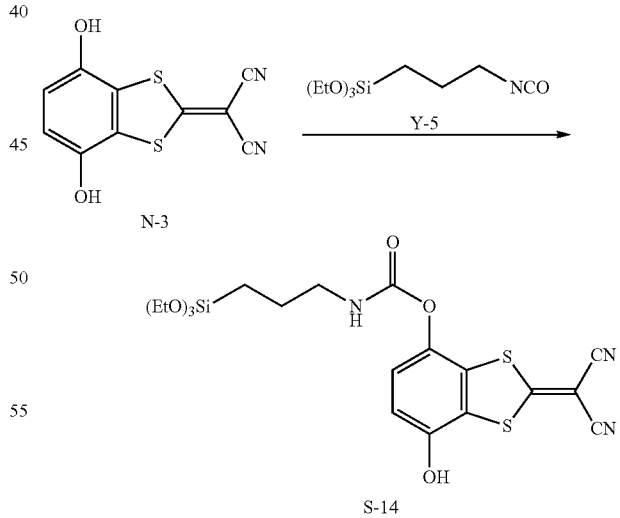

Under a nitrogen atmosphere, 1.00 g (moisture content: 2.8% by mass) of Exemplary Compound N-3 which is a compound represented by General Formula (W), 1.00 g of 3-triethoxysilylpropyl isocyanate (Y-5) which is a compound represented by General Formula (Y) and 4.0 mL of dry tetrahydrofuran were stirred, and one drop of dibutyltin dilaurate was added to this mixture. The mixture was reacted at 60° C. for 2 hours under a nitrogen atmosphere. Since the progress of the reaction was slow as compared with the time in the case where the high-purity Exemplary Compound N-3 was used and reacted for 2 hours, 1.00 g of 3-triethoxysilylpropyl isocyanate (Y-5) which is a compound represented by General Formula (Y) was added, and the mixture was further reacted at 60° C. for 2 hours. As a result of TLC analysis of the reaction mixture, the production of Exemplary Compound S-14 was confirmed.

By comparison with the case of using the low-purity Exemplary Compound N-3, it was found that, by using a high purity composition containing 90% by mass of the compound represented by General Formula (W) and having a moisture content of 2% by mass or less, the reaction rate in the reaction with the compound represented by General Formula (Y) having an isocyanato group can be accelerated. The reason for this is presumed to be that the decomposition of 3-triethoxysilylpropyl isocyanate (Y-5) due to water in the material could be suppressed.

<Synthesis of Exemplary Compound S-29 (Using High-Purity Exemplary Compound N-5)>

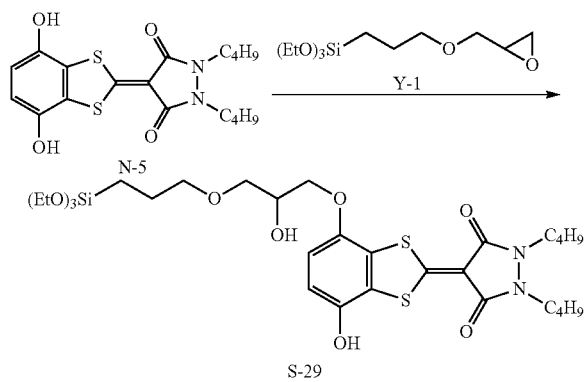

Under a nitrogen atmosphere, 0.62 g of γ-glycidyloxypropyltriethoxysilane (Y-1) which is a compound represented by General Formula (Y) was added to a mixture of 0.84 g (moisture content: 0.8% by mass) of Exemplary Compound N-5 which is a compound represented by General Formula (W), 18 mg of tetrabutylammonium iodide and 2.0 mL of dry butyl acetate, and the mixture was stirred with heating at 120° C. for 3 hours under a nitrogen atmosphere. The obtained reaction mixture was a homogeneous solution in which formation of insoluble matters could not be confirmed. The reaction mixture was concentrated and the proton NMR was measured. As a result, the production of Exemplary Compound S-29 which is a compound having a benzodithiol structure was confirmed.

$^1$H-NMR (CDCl$_3$) δ6.94 (br., 2H), 3.97-3.34 (m, 7H), 3.82 (t, 6H), 3.65 (t, 4H), 1.71 (m, 2H), 1.52 (m, 4H), 1.27 (m, 4H), 1.21 (t, 9H), 0.88 (t, 6H), 0.65 (t, 2H)

<Synthesis of Exemplary Compound S-29 (Using Low-Purity Exemplary Compound N-5)>

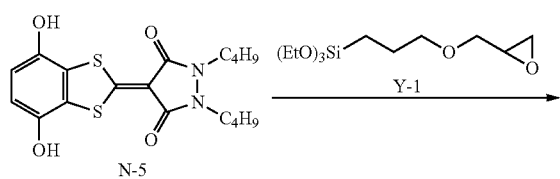

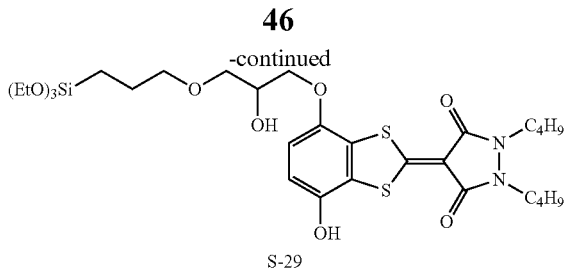

Under a nitrogen atmosphere, 0.62 g of γ-glycidyloxypropyltriethoxysilane (Y-1) which is a compound represented by General Formula (Y) was added to a mixture of 0.84 g (moisture content: 5.8% by mass) of Exemplary Compound N-5 which is a compound represented by General Formula (W), 18 mg of tetrabutylammonium iodide and 2.0 mL of dry butyl acetate, and the mixture was stirred with heating at 120° C. for 3 hours under a nitrogen atmosphere. In the resulting reaction mixture, a slight amount of insoluble matters was formed, unlike the case where the high-purity Exemplary Compound N-5 was used. The dissolved portion of the reaction mixture was concentrated and the proton NMR was measured. As a result, the production of Exemplary Compound S-29 which is a compound having a benzodithiol structure was confirmed.

By comparison with the case of using the low-purity Exemplary Compound N-5, it was found that, by using a high purity composition containing 90% by mass of the compound represented by General Formula (W) and having a moisture content of 2% by mass or less, the formation of insoluble matters in the reaction with the compound represented by General Formula (Y) having an epoxy group can be suppressed. The reason for this is presumed to be that the hydrolysis of the silyl group of γ-glycidyloxypropyltriethoxysilane due to water in the material could be suppressed.

<Synthesis of Exemplary Compound S-53>

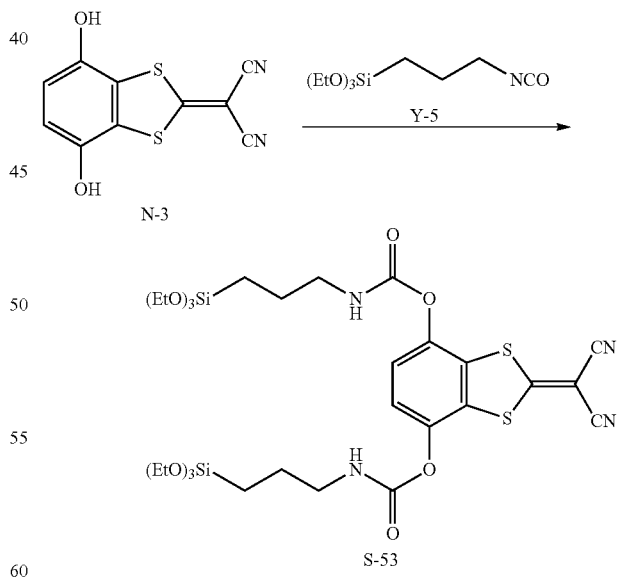

Under a nitrogen atmosphere, 1.00 g (moisture content: 0.1% by mass) of Exemplary Compound N-3 which is a compound represented by General Formula (W), 2.18 g of 3-triethoxysilylpropyl isocyanate (Y-5) which is a compound represented by General Formula (Y) and 4.0 mL of dry tetrahydrofuran were stirred, and one drop of dibutyltin dilaurate was added to this mixture. The mixture was reacted at 60° C. for 3 hours under a nitrogen atmosphere. The reaction mixture was concentrated, and the proton NMR was measured. As a result, the production of Exemplary Compound S-53, which is a compound having a benzodithiol structure, was confirmed. In addition, as a result of TLC analysis of the reaction mixture, the production of Exemplary Compound S-53 was supported (Rf value of Exemplary Compound N-3: 0.20, Rf value of Exemplary Compound S-53: 0.72, TLC plate: TLC silica gel 60F254 manufactured by Merck Corporation, Deployment solvent: ethyl acetate/n-hexane=1/1 by volume).

$^1$H-NMR (CDCl$_3$) δ7.34 (s, 2H), 5.77 (t, 2H), 3.87 (q, 12H), 3.31 (dt, 4H), 1.76 (m, 4H), 1.25 (t, 18H), 0.71 (t, 4H)

<Synthesis of Exemplary Compound S-54> gel 60F254 manufactured by Merck Corporation, Deployment solvent: ethyl acetate/n-hexane=1/1 by volume).

The mixture was reacted for another 2 hours at 60° C. The reaction mixture was concentrated, and the proton NMR was measured. As a result, the production of Exemplary Compound S-54, which is a compound having a benzodithiol structure, was confirmed. In addition, as a result of TLC analysis of the reaction mixture, the production of Exemplary Compound S-54 was supported (Rf value of Exemplary Compound S-54: 0.69, TLC plate: TLC silica gel 60F254 manufactured by Merck Corporation, Deployment solvent: ethyl acetate/n-hexane=1/1 by volume).

$^1$H-NMR (CDCl$_3$) δ7.21 (s, 1H), 5.88 (m, 2H), 3.88 (q, 12H), 3.30 (t, 4H), 2.26 (s, 3H), 1.79 (m, 4H), 1.25 (t, 18H), 0.72 (t, 4H)

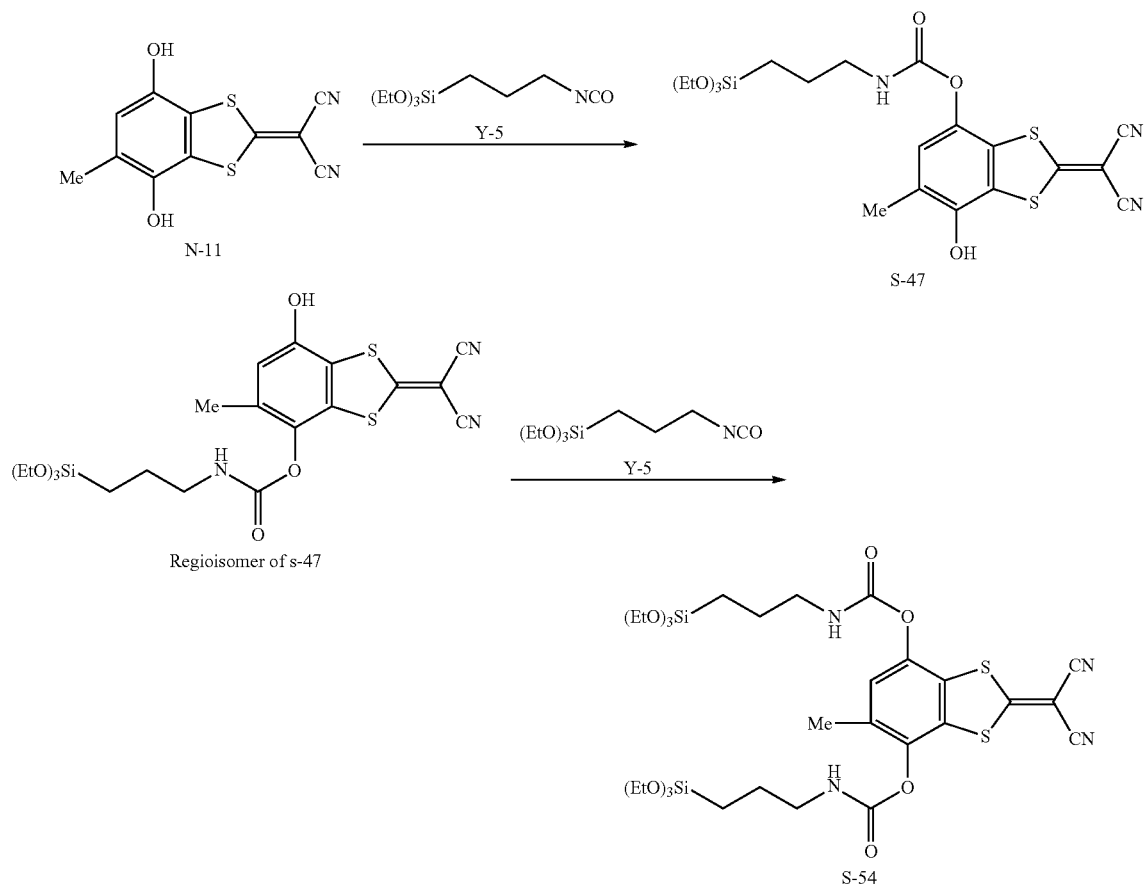

Under a nitrogen atmosphere, 1.05 g (moisture content: 0.05% by mass) of Exemplary Compound N-11 which is a compound represented by General Formula (W), 2.18 g of 3-triethoxysilylpropyl isocyanate (Y-5) which is a compound represented by General Formula (Y) and 4.0 mL of dry tetrahydrofuran were stirred, and one drop of dibutyltin dilaurate was added to this mixture. The mixture was reacted at 60° C. for 10 minutes under a nitrogen atmosphere. As a result of TLC analysis of the reaction mixture, the production of Exemplary Compound S-47 and a regioisomer thereof was confirmed (Rf value of Exemplary Compound N-11: 0.29, Rf Values of Exemplary Compound S-47 and a regioisomer thereof: 0.37 and 0.48, TLC plate: TLC silica <Synthesis of Exemplary Compound S-63>

Under a nitrogen atmosphere, 1.31 g (moisture content: 0.6% by mass) of Exemplary Compound N-32 which is a compound represented by General Formula (W), 0.56 g of 3-triethoxysilylpropyl isocyanate (Y-5) which is a compound represented by General Formula (Y) and 4.0 mL of dry tetrahydrofuran were stirred, and one drop of NEO-STANN U-600 (manufactured by Nitto Kasei Co., Ltd.) was added to this mixture. The mixture was reacted by heating under reflux for 3 hours under a nitrogen atmosphere. As a result of TLC analysis of the reaction mixture, the production of Exemplary Compound S-63 was supported (Rf value of Exemplary Compound N-32: 0.59, Rf value of Exemplary Compound S-63: 0.32, TLC plate: TLC silica gel 60F254 manufactured by Merck Corporation, Deployment solvent: ethyl acetate/n-hexane=1/1 by volume).

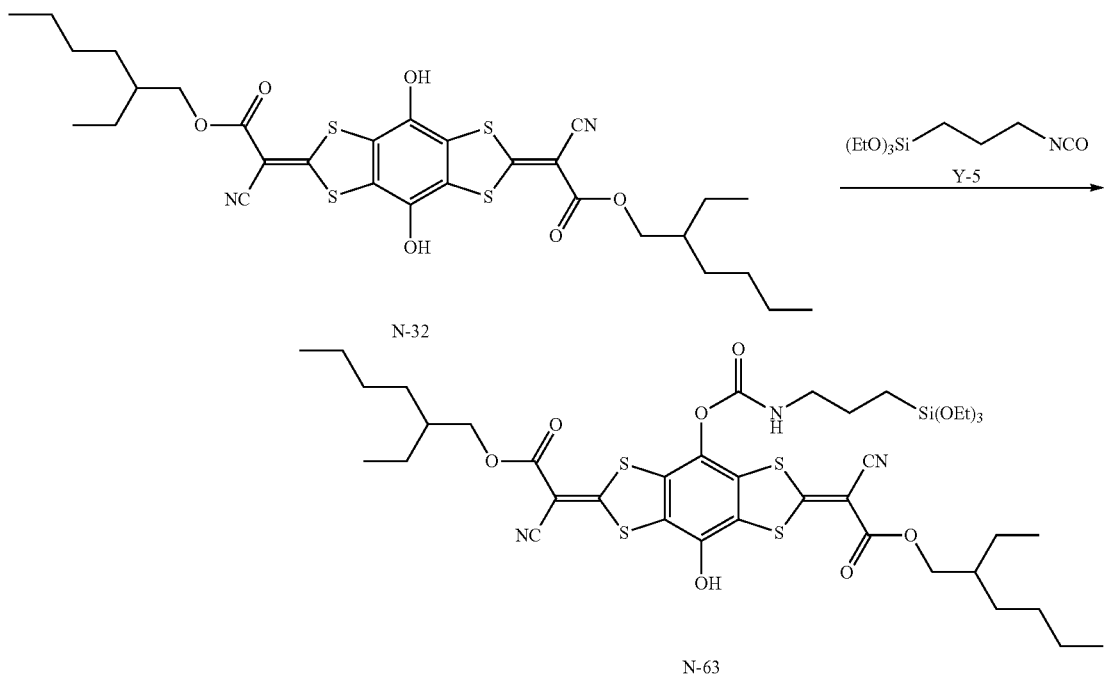

N-32

N-63

Example 1

<Preparation of Sol-Gel Film>

Under a nitrogen atmosphere, 1.20 g of Exemplary Compound N-5 which is a compound represented by General Formula (W), 2.71 g of 3-triethoxysilylpropyl isocyanate (Y-5) which is a compound represented by General Formula (Y), and 20 mL of dry tetrahydrofuran were stirred, and one drop of tin di(2-ethylhexanoate) was added to this mixture. The mixture was refluxed with heating under a nitrogen atmosphere for 3 hours to obtain a tetrahydrofuran solution (1A) containing Exemplary Compound S-21 which is a compound having a benzodithiol structure. Incidentally, this solution also contains Exemplary Compound N-5 and Exemplary Compound S-22.

81.0 mg of tetraethoxysilane and 0.602 g of glycidyloxypropyltrimethoxysilane, which are hydrolyzable silicon compounds, 1.73 g of ultrapure water and 17.0 mg of acetic acid which is an acid catalyst were added to 0.476 g of the tetrahydrofuran solution (1A) containing Exemplary Compound S-21 which is a compound having a benzodithiol structure. The obtained mixture was stirred for 30 seconds, irradiated with ultrasonic waves for 3 minutes, and stirred for 1 hour in a 50° C. bath to obtain a transparent pale yellow sol liquid (2A). This sol liquid (2A) was used as the composition of Example 1.

0.3 ml of the sol liquid (2A) was applied onto a glass substrate treated with 0.1% by mass KOH using a doctor blade of 30 mil (1 mil equals to $2.54 \times 10^{-5}$ m), and statically dried with a blast dryer at 80° C. for 30 minutes. This was followed by heating at 200° C. for 30 minutes to obtain a homogeneous and highly transparent sol-gel film (2C). This sol-gel film (2C) was used as the film of Example 1, and the obtained glass article was used as the glass article of Example 1.

Example 2

<Preparation of Sol-Gel Film>

0.3 mL of the sol liquid (2A) of Example 1 was applied onto a glass substrate treated with 0.1% by mass KOH using a doctor blade of 120 mil, and statically dried with a blast dryer at 80° C. for 30 minutes. This was followed by heating at 200° C. for 30 minutes to obtain a homogeneous and highly transparent sol-gel film (3C). This sol-gel film (3C) was used as the film of Example 2, and the obtained glass article was used as the glass article of Example 2.

Example 3

<Preparation of Sol-Gel Film>

Under a nitrogen atmosphere, 1.00 g of Exemplary Compound N-3 which is a compound represented by General Formula (W), 1.00 g of 3-triethoxysilylpropyl isocyanate (Y-5) which is a compound represented by General Formula (Y), and 4 mL of dry tetrahydrofuran were stirred, and one drop of dibutyltin dilaurate was added to this mixture. The mixture was stirred with heating at 60° C. for 2 hours under a nitrogen atmosphere to obtain a tetrahydrofuran solution (11A) containing Exemplary Compound S-14 which is a compound having a benzodithiol structure. Incidentally, this solution also contains Exemplary Compound N-3 and Exemplary Compound S-53.

200 mg of tetraethoxysilane and 0.221 g of glycidyloxypropyltriethoxysilane, which are hydrolyzable silicon compounds, 1.82 g of ultrapure water and 19.3 mg of acetic acid which is an acid catalyst were added to 0.101 g of the tetrahydrofuran solution (11A) containing Exemplary Compound S-14 which is a compound having a benzodithiol structure. The obtained mixture was stirred for 30 seconds, irradiated with ultrasonic waves for 3 minutes, and stirred for 1 hour in a 50° C. bath to obtain a transparent pale yellow sol liquid (11B). This sol liquid (11B) was used as the composition of Example 3.

0.3 ml of the sol liquid (11B) was applied onto a glass substrate treated with 0.1% by mass KOH using a doctor blade of 30 mil, and statically dried with a blast dryer at 80° C. for 30 minutes. This was followed by heating at 200° C. for 30 minutes to obtain a homogeneous and highly transparent sol-gel film (11C). This sol-gel film (11C) was used as the film of Example 3, and the obtained glass article was used as the glass article of Example 3.

Example 4

<Preparation of Sol-Gel Film>

Under a nitrogen atmosphere, 1.00 g of Exemplary Compound N-3 which is a compound represented by General Formula (W), 1.00 g of 3-triethoxysilylpropyl isocyanate (Y-5) which is a compound represented by General Formula (Y), and 4 mL of dry tetrahydrofuran were stirred, and one drop of dibutyltin dilaurate was added to this mixture. The mixture was stirred with heating at 60° C. for 2 hours under a nitrogen atmosphere.

1.19 g of 3-triethoxysilylpropyl isocyanate (Y-5) which is a compound represented by General Formula (Y) was added to this mixture which was then further stirred with heating at 60° C. for 2 hours under a nitrogen atmosphere to obtain a tetrahydrofuran solution (12A) containing Exemplary Compound S-53 which is a compound having a benzodithiol structure. Incidentally, this solution also contains Exemplary Compound S-14.

204 mg of tetraethoxysilane and 0.221 g of glycidyloxypropyltriethoxysilane, which are hydrolyzable silicon compounds, 1.91 g of ultrapure water and 17.8 mg of acetic acid which is an acid catalyst were added to 0.050 g of the tetrahydrofuran solution (12A) containing Exemplary Compound S-53 which is a compound having a benzodithiol structure. The obtained mixture was stirred for 30 seconds, irradiated with ultrasonic waves for 3 minutes, and stirred for 1 hour in a 50° C. bath to obtain a transparent pale yellow sol liquid (12B). This sol liquid (12B) was used as the composition of Example 4.

0.3 ml of the sol liquid (12B) was applied onto a glass substrate treated with 0.1% by mass KOH using a doctor blade of 15 mil, and statically dried with a blast dryer at 80° C. for 30 minutes. This was followed by heating at 200° C. for 30 minutes to obtain a homogeneous and highly transparent sol-gel film (12C). This sol-gel film (12C) was used as the film of Example 4, and the obtained glass article was used as the glass article of Example 4.

Example 5

<Preparation of Sol-Gel Film>

Under a nitrogen atmosphere, 1.05 g of Exemplary Compound N-11 which is a compound represented by General Formula (W), 1.10 g of 3-triethoxysilylpropyl isocyanate (Y-5) which is a compound represented by General Formula (Y), and 4 mL of dry tetrahydrofuran were stirred, and one drop of dibutyltin dilaurate was added to this mixture. The mixture was stirred with heating at 60° C. for 3 hours under a nitrogen atmosphere to obtain a tetrahydrofuran solution (13A) containing Exemplary Compound S-47 which is a compound having a benzodithiol structure and the compound which is a regioisomer thereof. Incidentally, this solution also contains Exemplary Compound N-11.

213 mg of tetraethoxysilane and 0.241 g of glycidyloxypropyltriethoxysilane, which are hydrolyzable silicon compounds, 1.88 g of ultrapure water and 17.5 mg of acetic acid which is an acid catalyst were added to 0.054 g of the tetrahydrofuran solution (13A) containing Exemplary Compound S-47 which is a compound having a benzodithiol structure and the compound which is a regioisomer thereof. The obtained mixture was stirred for 30 seconds, irradiated with ultrasonic waves for 3 minutes, and stirred for 30 minutes in a 50° C. bath to obtain a transparent pale yellow sol liquid (13B). This sol liquid (13B) was used as the composition of Example 5.

0.3 ml of the sol liquid (13B) was applied onto a glass substrate treated with 0.1% by mass KOH using a doctor blade of 15 mil, and statically dried with a blast dryer at 80° C. for 30 minutes. This was followed by heating at 200° C. for 30 minutes to obtain a homogeneous and highly transparent sol-gel film (13C). This sol-gel film (13C) was used as the film of Example 5, and the obtained glass article was used as the glass article of Example 5.

Comparative Example 1

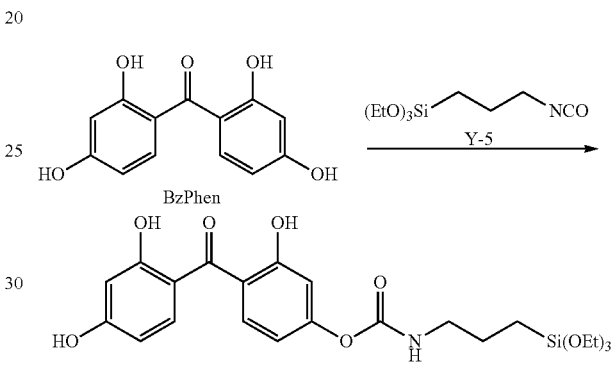

1.23 g of 2,2',4,4'-tetrahydroxybenzophenone (BzPhen), 2.47 g of 3-triethoxysilylpropyl isocyanate and 6.6 mL of dry tetrahydrofuran were stirred and one drop of tin di(2-ethylhexanoate) was added to this mixture. The mixture was refluxed with heating for 5 hours under a nitrogen atmosphere to obtain a tetrahydrofuran solution (1RA) containing 4-(3-triethoxysilylpropylaminocarbonyloxy)-2,2',4'-trihydroxybenzophenone.

0.396 g of the above tetrahydrofuran solution (1RA) containing 4-(3-triethoxysilylpropylaminocarbonyloxy)-2,2',4'-trihydroxybenzophenone, 73.8 mg of tetraethoxysilane, 0.185 g of glycidyloxypropyltrimethoxysilane, 1.78 g of ultrapure water and 10.0 mg of acetic acid were added and stirred for 30 seconds. This was followed by irradiation with ultrasonic waves for 3 minutes and stirring in a 50° C. bath for 1 hour to obtain a milky transparent sol liquid (2RA). This sol liquid (2RA) was used as the composition of Comparative Example 1.

0.3 mL of the sol liquid (2RA) was applied onto a glass substrate treated with 0.1% by mass KOH using a doctor blade of 30 mil, and statically dried with a blast dryer at 80° C. for 30 minutes. This was followed by heating at 200° C. for 30 minutes to obtain a homogeneous and highly transparent sol-gel film (2RC). This sol-gel film (2RC) was used as the film of Comparative Example 1, and the obtained glass article was used as the glass article of Comparative Example 1.

Comparative Example 2

0.3 mL of the sol liquid (2RA) prepared in Comparative Example 1 was applied onto a glass substrate treated with 0.1% by mass KOH using a doctor blade of 120 mil, and statically dried with a blast dryer at 80° C. for 30 minutes. This was followed by heating at 200° C. for 30 minutes to obtain a homogeneous and highly transparent sol-gel film (3RC). This sol-gel film (3RC) was used as the film of Comparative Example 2, and the obtained glass article was used as the glass article of Comparative Example 2.

Comparative Example 3

51.4 mg of 2,2',4,4'-tetrahydroxybenzophenone (BzPhen shown below), 86.1 mg of tetraethoxysilane, 0.601 g of glycidyloxypropyltriethoxysilane, 1.76 g of ultrapure water and 8.0 mg of acetic acid were added and stirred for 30 seconds. This was followed by irradiation with ultrasonic waves for 3 minutes and stirring in a 50° C. bath for 1 hour to obtain a milky transparent sol liquid (11RA). This sol liquid (11RA) was used as the composition of Comparative Example 3.

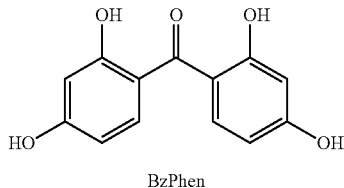 [SMILES: O=C(c1ccc(O)cc1O)c1ccc(O)cc1O]

BzPhen 0.3 mL of the sol liquid (11RA) was applied onto a glass substrate treated with 0.1% by mass KOH using a doctor blade of 30 mil, and statically dried with a blast dryer at 80° C. for 30 minutes. This was followed by heating at 200° C. for 30 minutes to obtain a homogeneous and highly transparent sol-gel film (11RC). This sol-gel film (11RC) was used as the film of Comparative Example 3, and the obtained glass article was used as the glass article of Comparative Example 3.

Comparative Example 4

A mixture of 1.00 g of 2,2',4,4'-tetrahydroxybenzophenone (BzPhen shown below), 1.21 g of glycidyloxypropyltriethoxysilane (Y-1 shown below), 36 mg of tetrabutylammonium iodide, and 4.0 mL of dry butyl acetate was stirred with heating at 120° C. for 4 hours under a nitrogen atmosphere to obtain a butyl acetate solution (12RS) containing 4-(2-hydroxy-(3-triethoxysilylpropyloxy)propyloxy)-2,2',4'-trihydroxybenzophenone having the structure shown below. Incidentally, this solution contains 2,2',4,4'-tetrahydroxybenzophenone.

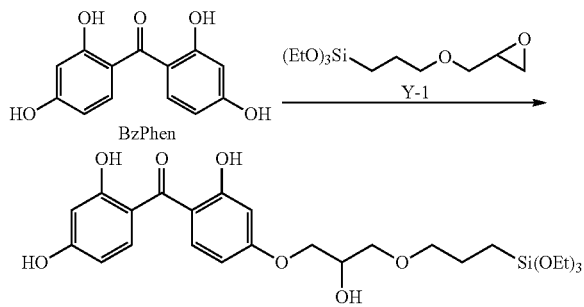

0.267 g of the above butyl acetate solution (12RS) containing 4-(2-hydroxy-(3-triethoxysilylpropyloxy)propyloxy)-2,2',4'-trihydroxybenzophenone, 84.3 mg of tetraethoxysilane, 0.626 g of glycidyloxypropyltriethoxysilane, 1.76 g of ultrapure water and 9.5 mg of acetic acid were added and stirred for 30 seconds. This was followed by irradiation with ultrasonic waves for 3 minutes and stirring in a 50° C. bath for 1 hour to obtain a milky transparent sol liquid (12RA). This sol liquid (12RA) was used as the composition of Comparative Example 4.

0.3 mL of the sol liquid (12RA) was applied onto a glass substrate treated with 0.1% by mass KOH using a doctor blade of 30 mil, and statically dried with a blast dryer at 80° C. for 30 minutes. This was followed by heating at 200° C. for 30 minutes to obtain a homogeneous and highly transparent sol-gel film (12RC). This sol-gel film (12RC) was used as the film of Comparative Example 4, and the obtained glass article was used as the glass article of Comparative Example 4.

[Evaluation]
<Spectrophotometric Measurement>

Absorption spectra of the sol-gel films (2C) and (3C) which are films of Examples 1 and 2 were measured using a spectrophotometer (UV-3100, product name, manufactured by Shimadzu Corporation). The results are shown in FIG. 1.

Absorption spectra of the sol-gel films (11C), (12C), and (13C) which are films of Examples 3 to 5 were measured using a spectrophotometer (UV-3100, product name, manufactured by Shimadzu Corporation). The results are shown in FIG. 2.

Figure 2:
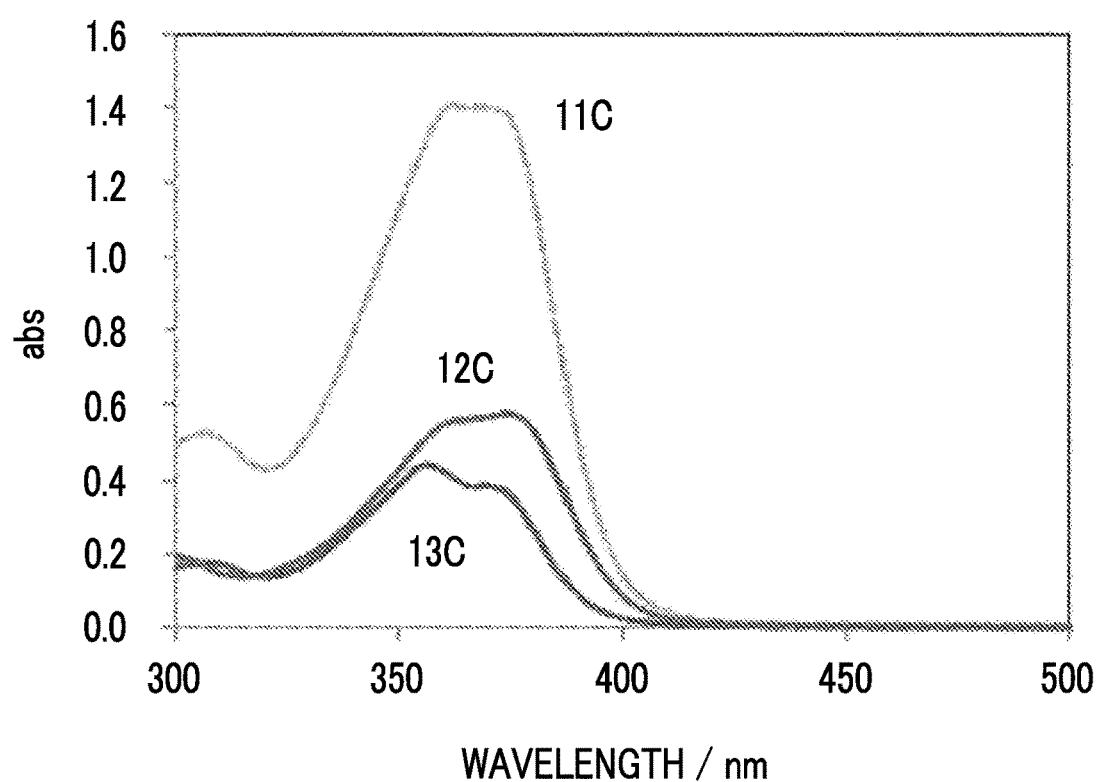
FIG. 2 shows absorption spectra of sol-gel films (11C), (12C), and (13C) which are films of Examples 3 to 5.

From the results of FIG. 1 and FIG. 2, it can be seen that the sol-gel films which are the films of the present invention are useful as an ultraviolet absorber-containing glass surface coating agent that has an absorption maximum wavelength in the long wavelength ultraviolet range (380 nm) and is capable of efficiently blocking long wavelength ultraviolet rays.

Similarly, absorption spectra of the sol-gel films (2RC), (3RC), (11RC), and (12RC) obtained in Comparative Examples 1 to 4 were measured. From the obtained absorption spectra, the absorption maximum wavelength and the ultraviolet range shielding properties (UV shielding properties) were determined. The results are shown in Table 1 below.

<Pencil Hardness>

The pencil hardness of the surface of the sol-gel film obtained in each Example and Comparative Example was measured according to JIS-K-5400.

The results are shown in Table 1 below.

<Light Fastness>

A glass filter (cut to 310 nm or less) was attached to a xenon lamp (manufactured by Ushio Inc., 500 W), and the sol-gel film obtained in each Example and Comparative Example was irradiated with light so that the incident light intensity was 80 mJ/cm$^2$. The residual amount of each of the ultraviolet absorbing compounds (compounds having a benzodithiol structure or benzophenone-based compounds used in Comparative Examples) after 120 hours was measured, and the light fastness was evaluated. The residual amount after aging was calculated according to the following equation.

Residual ratio (%)=(absorbance after irradiation)/(absorbance before irradiation)×100

The residual ratio is a value calculated by using the absorbance measured in terms of absorption maximum wavelength (also referred to as λmax) of the added compound. The results are shown in Table 1 below.

TABLE 1

| | Film (sol-gel film) | | Evaluation | | | |
|---|---|---|---|---|---|---|
| | Sol-gel film | Thickness on glass substrate (μm) | Absorption maximum wavelength (nm) | UV shielding properties (absorbance) | Pencil hardness | Light fastness (residual ratio (%)) |
| Example 1 | 2C | 30 | 380 | 1.04 | 4H | 80 |
| Example 2 | 3C | 120 | 380 | 3.61 | 4H | 92 |
| Example 3 | 11C | 30 | 370 | 1.40 | 5H | 76 |
| Example 4 | 12C | 15 | 375 | 0.44 | 5H | 75 |
| Example 5 | 13C | 15 | 355 | 0.58 | 5H | 73 |
| Comparative Example 1 | 2RC | 30 | 305 | 1.67 | 4H | 60 |
| Comparative Example 2 | 3RC | 120 | 305 | 2.17 | 4H | 59 |
| Comparative Example 3 | 11RC | 30 | 310 | 1.15 | 5H | 27 |
| Comparative Example 4 | 12RC | 30 | 305 | 0.90 | 4H | 30 |

From Table 1 above, it was found that the film of the present invention has long-wavelength ultraviolet range shielding properties, high pencil hardness and good light fastness. Therefore, it was found that the composition of the present invention is capable of providing a film having long-wavelength ultraviolet range shielding properties, high pencil hardness and good light fastness. That is, it was found that the composition of the present invention is useful for applications of glass surface coating agents and coating films, and in the case of being used for applications such as windowpanes for building materials and windowpanes for automobiles, the composition of the present invention is capable of satisfactorily exhibiting the effect of protection from sunburn.

On the other hand, according to Comparative Examples 1 to 4, the films using the composition not containing the compound having a benzodithiol structure have absorption maximum wavelengths of short wavelengths and low ultraviolet range shielding properties at long wavelengths, and from the viewpoint of protection from sunburn, they are not suitable for applications such as windowpanes for building materials and windowpanes for automobiles. It also proved to be poor in light fastness.

EXPLANATION OF REFERENCES

2C: Absorption spectrum of the sol-gel film (2C) which is the film of Example 1
3C: Absorption spectrum of the sol-gel film (3C) which is the film of Example 2
11C: Absorption spectrum of the sol-gel film (11C) which is the film of Example 3
12C: Absorption spectrum of the sol-gel film (12C) which is the film of Example 4
13C: Absorption spectrum of the sol-gel film (13C) which is the film of Example 5

What is claimed is:
1. A composition, comprising:
a compound having a benzodithiol structure and a silane coupling group; and
a compound having an —O—Si—O— structure,
wherein the compound having the benzodithiol structure and the silane coupling group is a compound represented by General Formula (I) or General Formula (II):

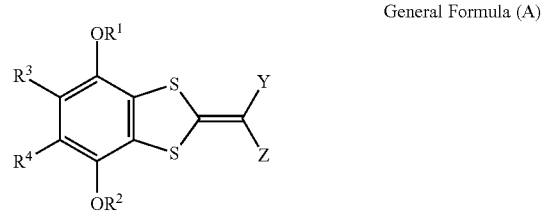

General Formula (A)

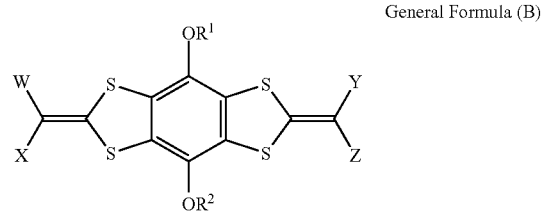

General Formula (B)

in General Formula (I) or General Formula (II), $R^1$ and $R^2$ each independently represent a hydrogen atom, an alkyl group, an aryl group, an acyl group, or a carbamoyl group, $R^3$ and $R^4$ each independently represent a hydrogen atom, a halogen atom, an alkyl group, an aryl group, an alkoxy group, or an aryloxy group, and W, X, Y, and Z each independently represent an electron withdrawing group; and W and X may be bonded to each other to form a ring, and Y and Z may be bonded to each other to form a ring; provided that $R^1$, $R^2$, $R^3$, $R^4$, W, X, Y, and Z may further have a substituent and at least one of $R^1$, $R^2$, $R^3$, $R^4$, W, X, Y, or Z contains the silane coupling group as a substituent,
wherein the silane coupling group is a trialkoxysilyl group, a dialkoxyalkylsilyl group, or an alkoxydialkylsilyl group,
wherein the compound having an —O—Si—O— structure as a hydrolyzable alkoxysilane is selected from the group consisting of tetramethoxysilane, tetraethoxysilane, tetra-n-propoxysilane, tetra-i-propoxysilane, tetra-n-butoxysilane, methyltrimethoxysilane, methyltriethoxysilane, ethyltrimethoxysilane, ethyltriethoxysilane, n-propyltrimethoxysilane, n-propyltriethoxysilane, phenyltrimethoxysilane, phenyltriethoxysilane, γ-glycidyloxypropyltrimethoxysilane, γ-glycidyloxypropyltriethoxyslane, γ-glycidyloxypropylmethyldimethoxysilane, γ-glycidyloxypropylmethyldiethoxysilane, γ-methacryloyloxypropyltrimethoxysilane, γ-methacryloyloxypropyltriethoxysilane, γ-methacryloyloxypropylmethyldimethoxysilane, vinyltrimethoxysilane, vinyltriethoxysilane, 3,4-epoxycyclohexylethyltrimethoxysilane, 3,4-epoxycyclohexylethyltriethoxysilane, tris-(trimethoxysilylpropyl)isocyanurate, 4-trimethoxysilylstyrene, 3,3,3-trifluoropropyltrimethoxysilane, dimethyldimethoxysilane, dimethyldiethoxysilane, diethyldimethoxysilane, diethyldiethoxysilane, di-n-propyldimethoxysilane, di-n-propyldiethoxysilane, diphenyldimethoxysilane, divinyldiethoxysilane, bis(triethoxysilylpropyl)tetrasulfide, 3-(trimethoxysilyl)propylisocyanate, and 3-(triethoxysilyl)propylisocyanate.

2. The composition according to claim 1, wherein, in General Formula (I) or General Formula (II), at least one of $R^1$ or $R^2$ is a hydrogen atom.

3. The composition according to claim 1, wherein, in General Formula (I) or General Formula (II), at least one of $R^1$ or $R^2$ is a carbamoyl group or an alkyl group, and $R^3$ and $R^4$ are hydrogen atoms.

4. The composition according to claim 1, wherein the silane coupling group is the trialkoxysilyl group.

5. A film having a polysiloxane structure and formed from the composition according to claim 1.

6. A glass article, comprising:
   a glass substrate; and
   the composition according to claim 1 positioned on at least a part of the glass substrate.

\* \* \* \* \*